United States Patent
Gannett et al.

(10) Patent No.: US 12,156,791 B2
(45) Date of Patent: Dec. 3, 2024

(54) CHITOSAN DRESSING FOR CONTROL OF BLEEDING IN TRANSURETHRAL PROSTATECTOMY

(71) Applicant: TRICOL BIOMEDICAL, INC., Portland, OR (US)

(72) Inventors: Cole Gannett, Portland, OR (US); Mattie R. Jones, Portland, OR (US); Ervelyn Winata, Portland, OR (US); Simon J. Mccarthy, Portland, OR (US)

(73) Assignee: TRICOL BIOMEDICAL, INC., Portland, OR (US)

( * ) Notice: Subject to any disclaimer, the term of this patent is extended or adjusted under 35 U.S.C. 154(b) by 989 days.

(21) Appl. No.: 16/958,307

(22) PCT Filed: Dec. 28, 2018

(86) PCT No.: PCT/US2018/067996
§ 371 (c)(1),
(2) Date: Jun. 26, 2020

(87) PCT Pub. No.: WO2019/133899
PCT Pub. Date: Jul. 4, 2019

(65) Prior Publication Data
US 2021/0059868 A1    Mar. 4, 2021

Related U.S. Application Data

(60) Provisional application No. 62/612,003, filed on Dec. 29, 2017.

(51) Int. Cl.
*A61F 13/00*    (2024.01)
*A61F 13/20*    (2006.01)
(Continued)

(52) U.S. Cl.
CPC .......... *A61F 13/36* (2013.01); *A61F 13/2025* (2013.01); *A61F 13/2071* (2013.01);
(Continued)

(58) Field of Classification Search
None
See application file for complete search history.

(56) References Cited

U.S. PATENT DOCUMENTS

| 7,371,403 B2 | 5/2008 | McCarthy et al. |
| 7,482,503 B2 | 1/2009 | Gregory et al. |

(Continued)

FOREIGN PATENT DOCUMENTS

| CA | 2669780 A1 | 5/2008 |
| CN | 101018554 A | 8/2007 |

(Continued)

OTHER PUBLICATIONS

WO 2013/180458 A1 Translation (Year: 2013).*
(Continued)

*Primary Examiner* — Kim M Lewis
(74) *Attorney, Agent, or Firm* — Seed IP Law Group LLP

(57) ABSTRACT

The present invention relates to a biocompatible, foldable, thin profile, low mass and high surface area, chitosan dressing, optionally modified with catechol, and suitable for treating bleeding in a physiological environment, e.g. bladder, and in particular in connection with the TURP procedure. The characteristics and structures of the chitosan dressing are provided. Methods of making and using the chitosan dressing are also provided.

2 Claims, 35 Drawing Sheets

(51) Int. Cl.
*A61F 13/26* (2006.01)
*A61F 13/36* (2006.01)
*A61F 13/15* (2006.01)
*A61L 15/28* (2006.01)
*A61L 15/44* (2006.01)

(52) U.S. Cl.
CPC ........ *A61F 13/2077* (2013.01); *A61F 13/266* (2013.01); *A61F 2013/15422* (2013.01); *A61F 2013/2014* (2013.01); *A61L 15/28* (2013.01); *A61L 15/44* (2013.01)

(56) References Cited

U.S. PATENT DOCUMENTS

| | | | |
|---|---|---|---|
| 7,820,872 | B2 | 10/2010 | Gregory et al. |
| 7,897,832 | B2 | 3/2011 | McAdams et al. |
| 8,269,058 | B2 | 9/2012 | McCarthy et al. |
| 8,313,474 | B2 | 11/2012 | Campbell et al. |
| 8,741,335 | B2 | 6/2014 | McCarthy |
| 8,920,514 | B2 | 12/2014 | Gregory et al. |
| 9,004,918 | B2 | 4/2015 | McAdams et al. |
| 9,204,957 | B2 | 12/2015 | Gregory et al. |
| 9,205,170 | B2 | 12/2015 | Lucchesi et al. |
| 10,086,105 | B2 | 10/2018 | Guo et al. |
| 10,315,023 | B2 | 6/2019 | Mantri et al. |
| 11,564,673 | B2 | 1/2023 | Perry et al. |
| 11,660,236 | B2 | 5/2023 | McCarthy et al. |
| 2004/0243043 | A1 | 12/2004 | McCarthy et al. |
| 2005/0038369 | A1 | 2/2005 | Gregory et al. |
| 2005/0137512 | A1 | 6/2005 | Campbell et al. |
| 2006/0089584 | A1 | 4/2006 | McAdams et al. |
| 2007/0166387 | A1 | 7/2007 | Ahuja et al. |
| 2008/0114286 | A1 | 5/2008 | Hamel et al. |
| 2008/0287907 | A1 | 11/2008 | Gregory et al. |
| 2009/0214712 | A1 | 8/2009 | Kang et al. |
| 2009/0226391 | A1 | 9/2009 | Roberts et al. |
| 2012/0065674 | A1 | 3/2012 | Levy |
| 2012/0296313 | A1 | 11/2012 | Andreacchi et al. |
| 2014/0193360 | A1 | 7/2014 | Lee et al. |
| 2015/0361218 | A1 | 12/2015 | Lee et al. |
| 2016/0030625 | A1 | 2/2016 | Mrozek et al. |
| 2018/0085500 | A1 | 3/2018 | Lee et al. |
| 2020/0306248 | A1 | 10/2020 | Beeley et al. |
| 2021/0052261 | A1 | 2/2021 | Perry et al. |
| 2021/0052766 | A1 | 2/2021 | Gannett et al. |
| 2021/0059867 | A1 | 3/2021 | Mccarthy et al. |
| 2021/0059868 | A1 | 3/2021 | Gannett et al. |
| 2021/0060203 | A1 | 3/2021 | Mccarthy et al. |
| 2023/0355224 | A1 | 11/2023 | Perry et al. |
| 2024/0009040 | A1 | 1/2024 | McCarthy et al. |

FOREIGN PATENT DOCUMENTS

| | | |
|---|---|---|
| CN | 103189435 A | 7/2013 |
| CN | 104013990 A | 9/2014 |
| CN | 106334209 A | 1/2017 |
| CN | 107118357 A | 9/2017 |
| CN | 107375196 A | 11/2017 |
| EP | 2700419 A1 | 2/2014 |
| EP | 2778179 A2 | 9/2014 |
| EP | 3300669 A1 | 4/2018 |
| GB | 2 514 592 A | 12/2014 |
| JP | 2005503197 A | 2/2005 |
| JP | 2007516051 A | 6/2007 |
| JP | 2008525112 A | 7/2008 |
| JP | 2009502749 A | 1/2009 |
| JP | 2009513239 A | 4/2009 |
| JP | 2016138166 A | 8/2016 |
| WO | WO 9736630 A1 | 10/1997 |
| WO | WO 02102276 A2 | 12/2002 |
| WO | WO 2005062896 A2 | 7/2005 |
| WO | WO 2006071649 A2 | 7/2006 |
| WO | WO 2007009050 A2 | 1/2007 |
| WO | WO 2007139845 A2 | 12/2007 |
| WO | WO 2009111282 A2 | 9/2009 |
| WO | WO-2013180458 A1 * | 12/2013 ............ A61L 15/44 |
| WO | WO 2015175662 A1 | 11/2015 |
| WO | WO 2016159734 A1 | 10/2016 |
| WO | WO 2017161331 A1 | 9/2017 |
| WO | WO 2017214201 A1 | 12/2017 |
| WO | WO 2018204782 A1 | 11/2018 |

OTHER PUBLICATIONS

Adler et al., "ASGE guideline: the role of endoscopy in acute non-variceal upper-GI hemorrhage," *Gastrointestinal Endoscopy* 60(4):497-504, 2004.

Banerjee et al., "The role of endoscopy in the management of patients with peptic ulcer disease," *Gastrointestinal Endoscopy* 71(4):663-668, 2010.

Boonpongmanee et al., "The frequency of peptic ulcer as a cause of upper-GI bleeding is exaggerated," *Gastrointestinal Endoscopy* 59(7):788-794, 2004.

Crooks et al., "Upper gastrointestinal haemorrhage and deprivation: a nationwide cohort study of health inequality in hospital admissions," *Gut* 61(4):514-520, 2012.

Elta et al., "Chapter 8: Approach to the patient with gross gastrointestinal bleeding," *Principles of Clinical Gastroenterology*:122-151, 2008.

Halkerston et al., "PWE-046 Early Clinical Experience of Endoclottm in the Treatment of Acute Gastro-Intestinal Bleeding," *Gut* 62(Suppl 1):A149, 2013.

HCUP, "Diagnoses—Clinical Classification Software (CCS), Principal Diagnosis: # 153 Gastrointestinal hemorrhage," U.S. Department of Health and Human Services, 2014. (1 page).

Holster et al., "Hemospray in the treatment of upper gastrointestinal hemorrhage in patients on antithrombotic therapy," *Endoscopy* 45:63-66, 2013.

Jairath et al., "Mortality from Acute Upper Gastrointestinal Bleeding in the United Kingdom: Does It Display a "Weekend Effect"?," *Am J Gastroenterol* 106:1621-1628, 2011.

Jairath et al., "Prevalence, management, and outcomes of patients with coagulopathy after acute nonvariceal upper gastrointestinal bleeding in the United Kingdom," *Transfusion* 53:1069-1076, 2013.

Jairath et al., "Why do mortality rates for nonvariceal upper gastrointestinal bleeding differ around the world? A systematic review of cohort studies," *Can J Gastroenterol* 26(8):537-543, 2012.

Karaman et al., "Endoscopic Topical Application of Ankaferd Blood Stopper® in Gastrointestinal Bleeding," *The Journal of Alternative and Complementary Medicine* 18(1):65-68, 2012.

Kheirabadi et al., "Safety Evaluation of New Hemostatic Agents, Smectite Granules, and Kaolin-Coated Gauze in a Vascular Injury Wound Model in Swine," *The Journal of Trauma Injury, Infection and Critical Care* 68(2):269-278, 2010.

Peng et al., "Factors Associated With Failure of Initial Endoscopic Hemoclip Hemostasis for Upper Gastrointestinal Bleeding," *J Clin Gastroenterol* 40(1):25-28, 2006.

Peng et al., "Factors Contributing to the Failure of Argon Plasma Coagulation Hemostasis in Patients with Nonvariceal Upper Gastrointestinal Tract Bleeding," *Hepato-Gastroenterology* 57:781-786, 2010.

Rockey, "Gastrointestinal bleeding," *Gastroenterol Clin North Am* 34:581-588, 2005.

Ryu et al., "Catechol-Functionalized Chitosan/Pluronic Hydrogels for Tissue Adhesives and Hemostatic Materials", *Biomacromolecules* 12:2653-2659, 2011.

Saraf et al., "Mechanical properties of soft human tissues under dynamic loading," *Journal of Biomechanics* 40:1960-1967, 2007.

Sheibani et al., "Natural history of acute upper GI bleeding due to tumours: short-term success and long-term recurrence with or without endoscopic therapy," *Aliment Pharmacol Ther* 38:144-150, 2013.

Sung et al., "Causes of Mortality in Patients With Peptic Ulcer Bleeding: A Prospective Cohort Study of 10,428 Cases," *Am J Gastroenterol* 105:84-89, 2010.

(56) References Cited

OTHER PUBLICATIONS

Sung et al., "Early clinical experience of the safety and effectiveness of Hemospray in achieving hemostasis in patients with acute peptic ulcer bleeding," *Endoscopy* 43:291-295, 2011.

Yau et al., "Safety and efficacy of Hemospray® in upper gastrointestinal bleeding," *Can J Gastroenterol Hepatol* 28(2):72-76, 2014.

AUA Practice Guidelines Committee, "AUA Guideline on Management of Benign Prostatic Hyperplasia (2003). Chapter 1: Diagnosis and Treatment Recommendations," *The Journal of Urology* 170:530-547, Aug. 2003.

CGI Environment Variables, URL=https://hcup-us.ahrq.gov/reports/natstats/his96/clinclas.htm (1996), download date Sep. 30, 2022.

Elixhauser et al., "Hospital Inpatient Statistics, 1996," HCUP-3 Research Note. Agency for Health Care Policy and Research, Rockville, MD, URL=https://hcup-us.ahrq.gov/reports/natstats/his96/clinclas.htm (1996), download date Sep. 30, 2022.

Fitzpatrick JM, M.W., Minimally invasive and endoscopic management of benign prostatic hyperplasia. Campbell's Urology, 2002. 8th edition (Walsh PC editor)(Saunders): p. 1379-1422.

HCUP, National Statistics Trend Information 1993-2010 Transurethral Prostatectomy and Open Prostatectomy, 2010, US Department of Health and Human Services.

HCUP, NIS 2003 Means on Continuous Fields in Core File. HCUP Summary Statistics Report, 2003: p. 27-8.

Kavanagh et al., "Prevention and management of TURP-related hemorrhage," *Nature Reviews Urology* 8:504-514, Sep. 2011.

Kim et al., "Chitosan-catechol: A polymer with long-lasting mucoadhesive properties," *Biomaterials* 52:161-170, Feb. 2015.

McVary et al., "Update on AUA Guideline on the Management of Benign Prostatic Hyperplasia," *The Journal of Urology* 185:1793-1803, May 2011.

Roberts, Chapter 5, "Chemical Behaviour of Chitin and Chitosan," Chitin Chemistry, 1992. (10 pages).

Ryu et al., "Bio-inspired adhesive catechol-conjugated chitosan for biomedical applications: A mini review," *Acta Biomaterialia* 27:101-115, 2015.

Ryu et al., "Bio-Inspired, Water-Soluble to Insoluble Self-Conversion for Flexible, Biocompatible, Transparent, Catecholamine Polysaccharide Thin Films," *Adv. Funt. Mater.* 24:7709-7716, 2014.

Subramanian et al., "Mucus interaction to improve gastrointestinal retention and pharmacokinetics of orally administered nano-drug delivery systems," *Journal of Nanobiotechnology* 20:362, Aug. 6, 2022. (23 pages).

Xu et al., "Mollusk Glue Inspired Mucoadhesives for Biomedical Applications," *Langmuir* 28:14010-14017, 2012.

Zeng et al., "Rapid in situ cross-linking of hydrogel adhesives based on thiol-grafted bio-inspired catechol-conjugated chitosan," *Biomaterials Processing* 32(5):612-621, 2017.

\* cited by examiner

| Batch # | Catechol CS ID# | CS Used | Starting % CS in soln. | mmol free amine | mmol HCA | mmol EDC HCl | mmol other |
|---|---|---|---|---|---|---|---|
| 1 | N/A | 65010 | ~0.5 | N/A | N/A | N/A | N/A |
| 2 | N/A | 43000 | 0.37 | N/A | N/A | N/A | N/A |
| 3 | N/A | 43000 | 0.48 | N/A | N/A | N/A | N/A |
| 4 | N/A | 65010 | ~0.5 | N/A | N/A | N/A | N/A |
| 5 | N/A | 65010 | ~0.5 | N/A | N/A | N/A | N/A |
| 6 | N/A | 43000 | 0.42 | N/A | N/A | N/A | N/A |
| 7 | N/A | 43000 | ~0.5 | N/A | N/A | N/A | N/A |
| 8 | N/A | 43000 | ~0.5 | N/A | N/A | N/A | N/A |
| 9 | N/A | 43000 | 0.29 | N/A | N/A | N/A | N/A |
| 10 | N/A | 43000 | 0.72 | N/A | N/A | N/A | N/A |
| 11 | N/A | 43000 | 0.51 | N/A | N/A | N/A | N/A |
| 12 | N/A | 43000 | ~0.5 | N/A | N/A | N/A | N/A |
| 13 | N/A | 43000 | 0.69 | N/A | N/A | N/A | NA |
| 14 | N/A | 65010 | 0.46 | N/A | N/A | N/A | NA |
| 15 | N/A | 43000 | 0.42 | N/A | N/A | N/A | N/A |
| 16 | N/A | 43000 | 1.8 | N/A | N/A | N/A | N/A |
| 17 | N/A | 43000 | ~0.5 | N/A | N/A | N/A | N/A |
| 18 | N/A | 43000 | ~0.5 | N/A | N/A | N/A | N/A |
| 19 | N/A | 43000 | ~0.5 | N/A | N/A | N/A | N/A |
| 20 | N/A | 43000 | ~0.5 | N/A | N/A | N/A | N/A |
| 21 | 21 | 43000 | 1.8 | 52.6 | 15.7 | 31.3 | N/A |
| 22 | 22 | 43000 | 0.5 | 2.94 | 2.96 | 5.94 | N/A |
| 23 | 23 | 43000 | 0.5 | 2.94 | 2.95 | 5.92 | N/A |
| 24 | 24 | 43000 | 0.5 | 2.92 | 2.95 | 5.97 | N/A |
| 25 | 25 | 43000 | 0.5 | 2.95 | 2.98 | 6.01 | N/A |
| 26 | 26 | 43000 | 0.5 | 6.20 | 5.91 | 11.82 | N/A |
| 27 | 27 | 43000 | 0.5 | 2.92 | 0.76 | 2.97 | 0.79 mmol NAC, 7.36 mmol NHS |
| 28 | CS-cat, 28 | 43000 | 0.5 | 2.95 | 0.77 | 2.96 | N/A |
| 29 | CS-cat, 29 | 43000 | 0.5 | | | | |

FIG. 14A

| Batch # | Catechol CS ID# | CS Used | Starting % CS in soln. | mmol free amine | mmol HCA | mmol EDC HCl | mmol other |
|---|---|---|---|---|---|---|---|
| 30 | CS-cat, 30 | 43000 | 0.5 | 2.93 | 1.48 | 2.93 | N/A |
| 31 | CS-cat, 31 | 43000 | 0.5 | 8.74 | 10.39 | 12.98 | N/A |
| 32 | CS-cat, 32 | 43000 | 0.5 | 8.76 | 10.41 | 12.98 | N/A |
| 33 | CS-cat, 33 | 43000 | 0.5 | 2.95 | 1.49 | 2.94 | N/A |
| 34 | CS-cat, 34 | 43000 | 0.5 | 2.96 | 0.85 | 2.97 | 0.81 mmol NAC |
| 35 | CS-cat, 35 | 43000 | 0.5 | 8.75 | 2.39 | 8.76 | 2.36 mmol NAC |
| 36 | CS-cat, 36 | 43000 | 0.5 | 8.74 | 1.48 | 2.95 | N/A |
| 37 | CS-cat, 37 | 43000 | 0.5 | 8.73 | 10.41 | 12.99 | N/A |
| 38 | CS-cat, 38 | 43000 | 0.5 | 8.74 | 1.47 | 2.96 | N/A |
| 39 | CS-cat, 39 | 43000 | 0.5 | 8.74 | 2.39 | 8.75 | 2.40 mmol NAC |
| 40 | CS-cat, 40 | 43000 | 0.5 | 8.75 | 1.47 | 2.95 | N/A |
| 41 | CS-cat, 41 | 43000 | 0.5 | 8.79 | 1.48 | 2.96 | N/A |

*FIG. 14B*

| Dressing Preparation # | Formulation type | CS | CAT %Deg Subst. | %solute (w/w) in soln. | Mold pour depth (mm) | Estimated compress (mm) | Compressed Dressing ρ (g/cm2) | Compressed dressing information |
|---|---|---|---|---|---|---|---|---|
| 1 | 2% CS, 2% acetic acid (Control) | 65010 | N/A | 2 | 5 | 0.2 | 0.63 | |
| 2 | 100% CS-Cat, 1 | 65010 | NA | - | 5 | 0.1 | - | |
| 3 | 100% CS-Cat, 1 | 65010 | NA | - | 5 | 0.2 | - | |
| 4 | 100% CS-Cat, 2 | 43000 | 21.8 | 0.4 | 5 | 0.1 | 0.21 | |
| 5 | 25:75 CS-Cat, 2 | 43000 | 21.8 | - | 5 | 0.1 | - | |
| 6 | 50:50 CS-Cat, 2 | 43000 | 21.8 | - | 5 | 0.1 | - | |
| 7 | 75:25 CS-Cat, 2 | 43000 | 21.8 | - | 5 | 0.1 | - | |
| 8 | 100% CS-Cat, 3 | 43000 | 11.5 | 0.5 | 5 | 0.1 | 0.25 | |
| 9 | 50:50 CS-Cat, 3 | 43000 | 11.5 | - | 5 | 0.1 | - | |
| 10 | 75:25 CS-Cat, 3 | 43000 | 11.5 | 0.5 | 5 | 0.1 | 0.25 | |
| 11 | 100% CS-Cat, 3 | 43000 | 11.5 | - | 5 | 0.1 | - | |
| 12 | 50:50 CS-Cat, 3 | 43000 | 11.5 | - | 5 | 0.1 | - | |
| 13 | 75:25 CS-Cat, 3 | 43000 | 11.5 | - | 5 | 0.1 | - | |
| 14 | Chitosan Lactate/Acetate | 65010 | - | 2.8 | 3 | 0.15 | 0.56 | |
| 15 | Chitosan, HPMC (90/10) | 65010 | - | 2.6 | 3 | 0.15 | 0.6 | |
| 16 | 2% CS, 2% acetic acid | 65010 | - | 2 | 3 | 0.1 | 0.6 | > 98% dry |
| 17 | 2% CS, 0.2% acetic acid | 65010 | - | 2 | 3 | 0.1 | 0.63 | |
| 18 | Chitosan, Polaxamer 90/10 | 65010 | - | 2.5 | 3 | 0.12 | 0.55 | |
| 19 | Chitosan: Sucrose 0.05% | 65010 | - | 2.2 | 3 | 0.12 | 0.6 | |
| 20 | Chitosan: Sucrose 0.1% | 65010 | - | 2 | 3 | 0.1 | | |

FIG. 14C

| Dressing Preparation # | Formulation type | CS | CAT %Deg Subst. | %solute (w/w) in soln. | Mold pour depth (mm) | Estimated compress (mm) | Compressed Dressing ρ (g/cm2) | Compressed dressing information |
|---|---|---|---|---|---|---|---|---|
| 21 | 25:75 CS-Cat, 4:CS lactate/acetate | 43000 | 11.5 | - | 3 | 0.1 | | |
| 22 | 50:50 CS-Cat, 4:CS lactate/acetate | 43000 | 11.5 | - | 3 | 0.1 | | |
| 23 | 75:25 CS-Cat, 4:CS lactate/acetate | 43000 | 11.5 | - | 3 | 0.1 | | |
| 24 | 2% CS, 0.222% HPC | 65010 | - | 2.5 | 3 | 0.12 | 0.63 | |
| 25 | 2% CS, 0.222% HEC | 65010 | - | 2.5 | 3 | 0.12 | 0.63 | |
| 26 | 2% CS Control | 65010 | - | 2 | 3 | 0.1 | 0.6 | |
| 27 | 1% CS, 0.05% Sucrose | 65010 | - | 2 | 2 | 0.05 | 0.8 | |
| 28 | 2% CS, 0.05% Sorbitol | 65010 | - | 2 | 2 | 0.05 | 0.8 | |
| 29 | CS-catechol, batch 6 | 43000 | 7.5 | 0.4 | 3 | 0.05 | 0.24 | |
| 30 | CS-catechol, batch 8 | 43000 | - | - | 3 | 0.05 | | |
| 31 | CS-catechol, batch 9 | 43000 | - | 0.3 | 3 | 0.05 | 0.18 | |
| 32 | CS-catechol, batch 10 | 43000 | 17 | 0.7 | 3 | 0.05 | 0.42 | |
| 33 | CS-catechol, batch 11 | 43000 | 26 | 0.5 | 2 | 0.05 | 0.2 | |
| 34 | CS-catechol, Batch 12 | 43000 | - | - | 2 | 0.05 | | |
| 35 | CS-catechol, batch13 | 43000 | - | 0.7 | 3 | 0.05 | 0.42 | |
| 36 | CS-catechol, batch 14 | 65010 | - | 0.5 | 3 | 0.05 | 0.3 | |
| 37 | CS-catechol, batch 15 | 43000 | - | 0.4 | 3 | 0.05 | 0.24 | |
| 38 | CS-catechol, batch 16 | 43000 | 29 | 0.6 | 3 | 0.05 | 0.36 | |

FIG. 14D

| Dressing Preparation # | Formulation type | CS | CAT %Deg Subst. | %solute (w/w) in soln. | Mold pour depth (mm) | Estimated compress (mm) | Compressed Dressing ρ (g/cm2) | Compressed dressing information |
|---|---|---|---|---|---|---|---|---|
| 39 | CS-catechol, batch 16 | 43000 | 26 | 1.8 | 3 | 0.07 | 0.77 | |
| 40 | CS-catechol, batch 17 | 43000 | - | 0.6 | 3 | 0.05 | 0.36 | |
| 41 | CS-catechol, batch 18 | 43000 | - | 0.7 | 2 | 0.05 | 0.28 | |
| 42 | CS-catechol, batch 19 | 43000 | - | 0.5 | 2 | 0.05 | 0.20 | |
| 43 | CS-catechol, batch 20 | 43000 | - | - | 3 | 0.05 | | |
| 44 | CS-catechol, batch 21 | 43000 | - | - | 3 | 0.07 | | |
| 45 | CS-catechol, batch 22-1 | 43000 | 7 | 1.6 | 3 | 0.07 | 0.68 | |
| 46 | CS-catechol, batch 22-2 | 43000 | - | 1.1 | 3 | 0.05 | 0.66 | |
| 47 | CS-catechol, batch 23 | 43000 | 13 | 0.4 | 3 | 0.05 | 0.24 | |
| 48 | CS-catechol, batch 24 | 43000 | 20 | 0.3 | 3 | 0.05 | 0.18 | |
| 49 | CS-catechol, batch 25 | 43000 | 15 | 0.4 | 3 | 0.05 | 0.24 | |
| 50 | CS-catechol, batch 26 | 43000 | 25 | 0.35 | 10 | 0.05 | 0.7 | |
| 51 | CS-catechol, batch 27 | 43000 | 18 | 0.3 | 10 | 0.05 | 0.6 | |
| 52 | CS-catechol, batch 26 | 43000 | 25 | 1.0 | 4 | 0.05 | 0.8 | |
| 53 | CS-catechol, batch 25 | 43000 | 15 | 2.0 | 2 | 0.05 | 0.8 | |
| 54 | CS-catechol, batch 28 | 43000 | 26 | 0.3 | 5 | 0.05 | 0.3 | |
| 55 | 50/50 CS-cat, 28/CS | 43000 | - | 0.5 | 5 | 0.05 | 0.5 | |
| 56 | 65/35 CS-cat, 28/CS | 43000 | - | 0.5 | 5 | 0.05 | 0.5 | |
| 57 | CS-catechol, batch 29 | 43000 | - | 0.3 | 5 | 0.05 | 0.3 | |
| 58 | CS-catechol, thiolated | 43000 | 21 | 0.35 | 5 | 0.05 | 0.7 | |
| 59 | 50/50 CS-cat, thiolated/CS | 43000 | - | 0.5 | 5 | 0.05 | 0.5 | |

FIG. 14E

| Dressing Preparation # | Formulation type | CS | CAT %Deg Subst. | %solute (w/w) in soln. | Mold pour depth (mm) | Estimated compress (mm) | Compressed Dressing ρ (g/cm2) | Compressed dressing information |
|---|---|---|---|---|---|---|---|---|
| 60 | 65/35 CS-cat, thiolated/CS | 43000 | - | 0.5 | 5 | 0.05 | 0.5 | |
| 61 | 51/49 CS-cat, thiolated/CS | 43000 | - | 0.5 | 5 | 0.05 | 0.5 | |
| 62 | 75/25 CS-cat, thiolated/CS | 43000 | - | 0.5 | 5 | 0.05 | 0.5 | |
| 63 | CS-catechol, batch 30 | 43000 | 21.74 | 0.5 | 5 | 0.05 | 0.5 | |
| 64 | CS-catechol, batch 31a | 43000 | - | 0.4 | 5 | 0.05 | 0.4 | |
| 65 | CS-catechol, batch 31b | 43000 | - | 0.4 | 5 | 0.05 | 0.4 | |
| 66 | CS-catechol, batch 31c | 43000 | - | 0.4 | 5 | 0.05 | 0.4 | |
| 67 | CS-catechol, batch 32 | 43000 | - | 0.5 | 7 | 0.05 | 0.7 | |
| 68 | CS-catechol, batch 32 | 43000 | - | 0.5 | 7 | 0.05 | 0.7 | |
| 69 | CS-catechol, batch 32 | 43000 | - | 0.5 | 7 | 0.05 | 0.7 | |
| 70 | CS-catechol, batch 32 | 43000 | - | 0.5 | 8 | 0.05 | 0.8 | |
| 71 | CS-catechol, batch 32 | 43000 | - | 0.5 | 7 | 0.05 | 0.7 | CS backed |
| 72 | 65/35 CS-cat, 32/CS | 43000 | - | 0.5 | 5 | 0.05 | 0.5 | |
| 73 | 50/50 CS-cat, 32/CS | 43000 | - | 0.5 | 5 | 0.05 | 0.5 | |
| 74 | 70/30 CS-cat, 32/CS | 43000 | - | 0.5 | 5 | 0.05 | 0.5 | |
| 75 | CS-catechol, batch 33 | 43000 | - | 0.5 | 5 | 0.05 | 0.5 | |
| 76 | CS-catechol, batch 34 | 43000 | - | 0.5 | 5 | 0.05 | 0.5 | |
| 77 | CS-catechol, batch 35 | 43000 | - | 0.5 | 5 | 0.05 | 0.5 | |
| 78 | 70/30 CS-cat 35/CS | 43000 | - | 0.5 | 5 | 0.05 | 0.5 | |
| 79 | 70/30 CS-cat 35/CS | 43000 | - | 0.5 | 5 | 0.05 | 0.5 | CS backed |
| 80 | CS-catechol, batch 36 | 43000 | - | 0.5 | 3 | 0.05 | 0.3 | CS backed |

FIG. 14F

| Dressing Preparation # | Formulation type | CS | CAT %Deg Subst. | %solute (w/w) in soln. | Mold pour depth (mm) | Estimated compress (mm) | Compressed Dressing ρ (g/cm2) | Compressed dressing information |
|---|---|---|---|---|---|---|---|---|
| 81 | CS-catechol, batch 37 | 43000 | - | 0.5 | 5 | 0.05 | 0.5 | |
| 82 | CS-catechol, batch 38 | 43000 | - | 0.5 | 5 | 0.05 | 0.5 | |
| 83 | 70/30 CS-catechol, batch 39/CS | 43000 | - | 0.5 | 5 | 0.05 | 0.5 | CS backed |
| 84 | CS-catechol, batch 40 | 43000 | - | 0.5 | 5 | 0.05 | 0.5 | CS backed |
| 85 | CS-catechol, batch 41 | 43000 | - | 0.5 | 5 | 0.05 | 0.5 | CS backed |

FIG. 14G

| Dressing Preparation # | Formulation type | Time to dissolution (hours) | Foldability F = Fail P = Pass | Burst Testing | Ex-Vivo | Accelerated Stability | In-Vivo |
|---|---|---|---|---|---|---|---|
| 1 | 2% CS, 2% acetic acid (Co-rol) | 2 | F | - | - | - | - |
| 2 | 100% CS-Cat, 1 | - | P | - | - | - | - |
| 3 | 100% CS-Cat, 1 | - | P | - | - | - | - |
| 4 | 100% CS-Cat, 2 | 61.7 | P | - | - | - | - |
| 5 | 25:75 CS-Cat, 2 | 15.6 | P | - | - | - | - |
| 6 | 50:50 CS-Cat, 2 | 35.7 | P | - | - | - | - |
| 7 | 75:25 CS-Cat, 2 | 168 | P | - | - | - | - |
| 8 | 100% CS-Cat, 3 | - | P | - | - | - | - |
| 9 | 50:50 CS-Cat, 3 | 27 | P | - | - | - | - |
| 10 | 75:25 CS-Cat, 3 | 57.8 | P | - | - | - | - |
| 11 | 100% CS-Cat, 3 | 68.8 | P | - | - | - | - |
| 12 | 50:50 CS-Cat, 3 | 31.7 | P | - | - | - | - |
| 13 | 75:25 CS-Cat, 3 | 68.5 | P | - | - | - | - |
| 14 | Chitosan Lactate/Acetate | 5.8 | F | - | - | - | - |
| 15 | Chitosan, HPMC (90/10) | 2.8 | F | - | - | - | - |
| 16 | 2% CS, 2% acetic acid | 0.7 | F | - | - | - | - |
| 17 | 2% CS, 0.2% acetic acid | 1.8 | F | - | - | - | - |
| 18 | Chitosan, Polaxamer 90/10 | 1.5 | F | - | - | - | - |
| 19 | Chitosan: Sucrose 0.05% | 6.7 | F | - | - | - | - |
| 20 | Chitosan: Sucrose 0.1% | 1 | F | - | - | - | - |

FIG. 15A

| Dressing Preparation # | Formulation type | Time to dissolution (hours) | Foldability F = Fail P= Pass | Burst Testing | Ex-Vivo | Accelerated Stability | In-Vivo |
|---|---|---|---|---|---|---|---|
| 21 | 25:75 CS-Cat, 4:CS lactate/acetate | 2 | P | - | - | - | - |
| 22 | 50:50 CS-Cat, 4:CS lactate/acetate | 2 | P | - | - | - | - |
| 23 | 75:25 CS-Cat, 4:CS lactate/acetate | 2 | P | - | - | - | - |
| 24 | 2% CS, 0.222% HPC | - | F | - | - | - | - |
| 25 | 2% CS, 0.222% HEC | - | F | - | - | - | - |
| 26 | 2% CS Co-rol | - | F | - | - | - | - |
| 27 | 1% CS, 0.05% Sucrose | 6.7 | F | - | - | - | - |
| 28 | 2% CS, 0.05% Sorbitol | 19 | F | - | - | - | - |
| 29 | CS-catechol, batch 6 | 120 | P | - | - | - | - |
| 30 | CS-catechol, batch 8 | 92 | P | - | - | - | - |
| 31 | CS-catechol, batch 9 | NA | P | - | - | - | - |
| 32 | CS-catechol, batch 10 | 16.3 | P | - | - | - | - |
| 33 | CS-catechol, batch 11 | 26 | P | - | - | - | - |
| 34 | CS-catechol, Batch 12 | NA | P | - | - | - | - |
| 35 | CS-catechol, batch13 | 27 | P | - | - | - | - |
| 36 | CS-catechol, batch 14 | 46 | P | - | - | - | - |
| 37 | CS-catechol, batch 15 | 27 | P | - | - | - | - |
| 38 | CS-catechol, batch 16 | - | P | - | - | - | - |
| 39 | CS-catechol, batch 16 | 32 | F | - | - | - | - |
| 40 | CS-catechol, batch 17 | 20 | P | - | - | - | - |

*FIG. 15B*

| Dressing Preparation # | Formulation type | Time to dissolution (hours) | Foldability F = Fail P = Pass | Burst Testing | Ex-Vivo | Accelerated Stability | In-Vivo |
|---|---|---|---|---|---|---|---|
| 41 | CS-catechol, batch 18 | 57.8 | P | - | - | - | - |
| 42 | CS-catechol, batch 19 | 13.6 | P | - | - | - | - |
| 43 | CS-catechol, batch 20 | 23 | P | - | - | - | - |
| 44 | CS-catechol, batch 21 | 71.7 | P | - | - | - | - |
| 45 | CS-catechol, batch 22-1 | 46 | P | - | - | - | - |
| 46 | CS-catechol, batch 22-2 | 71 | P | - | - | - | - |
| 47 | CS-catechol, batch 23 | 24 | P | - | - | - | - |
| 48 | CS-catechol, batch 24 | 23 | P | - | - | - | - |
| 49 | CS-catechol, batch 25 | 14.8 | P | - | - | - | - |
| 50 | CS-catechol, batch 26 | - | P | - | - | - | - |
| 51 | CS-catechol, batch 27 | - | P | - | - | - | - |
| 52 | CS-catechol, batch 26 | - | P | - | - | - | - |
| 53 | CS-catechol, batch 25 | - | P | - | - | - | - |
| 54 | CS-catechol, batch 28 | - | P | - | - | - | - |
| 55 | 50/50 CS-cat, 28/CS | 65 | P | - | - | - | - |
| 56 | 65/35 CS-cat, 28/CS | 44 | P | - | - | - | - |
| 57 | CS-catechol, batch 29 | - | P | - | - | - | - |
| 58 | CS-catechol, thiolated | 47 | P | - | - | - | - |
| 59 | 50/50 CS-cat, thiolated/CS | - | P | - | - | - | - |
| 60 | 65/35 CS-cat, thiolated/CS | 84.2 | P | - | - | - | - |

FIG. 15C

| Dressing Preparation # | Formulation type | Time to dissolution (hours) | Foldability F = Fail P = Pass | Burst Testing | Ex-Vivo | Accelerated Stability | In-Vivo |
|---|---|---|---|---|---|---|---|
| 61 | 51/49 CS-cat, thiolated/CS | 43.3 | P | - | - | - | - |
| 62 | 75/25 CS-cat, thiolated/CS | 71 | P | - | - | - | - |
| 63 | CS-catechol, batch 30 | 90 | P | - | - | - | - |
| 64 | CS-catechol, batch 31a | 156.7 | P | - | - | - | - |
| 65 | CS-catechol, batch 31b | 133.3 | P | - | - | - | - |
| 66 | CS-catechol, batch 31c | 122 | P | - | - | - | - |
| 67 | CS-catechol, batch 32 | 128.3 | P | - | - | - | - |
| 68 | CS-catechol, batch 32 | 144.5 | P | - | - | - | - |
| 69 | CS-catechol, batch 32 | 200 | P | - | - | - | - |
| 70 | CS-catechol, batch 32 | 240 | P | - | - | - | A, Acute In-Vivo 1 |
| 71 | CS-catechol, batch 32 | 215 | P w/backing | - | - | - | - |
| 72 | 65/35 CS-cat, 32/CS | 107.6 | P | - | - | - | - |
| 73 | 50/50 CS-cat, 32/CS | 9.5 | P | - | - | - | C, Acute In-Vivo 1 |
| 74 | 70/30 CS-cat, 32/CS | 142 | P | - | - | - | - |
| 75 | CS-catechol, batch 33 | 109.8 | P | - | - | - | - |
| 76 | CS-catechol, batch 34 | - | P | - | - | - | - |
| 77 | CS-catechol, batch 35 | - | - | - | - | - | B, Acute In-Vivo 1 |
| 78 | 70/30 CS-cat 35/CS | 66 | P | - | - | - | - |

FIG. 15D

| Dressing Preparation # | Formulation type | Time to dissolution (hours) | Foldability F = Fail P= Pass | Burst Testing | Ex-Vivo | Accelerated Stability | In-Vivo |
|---|---|---|---|---|---|---|---|
| 79 | 70/30 CS-cat 35/CS | 59.3 | P | - | - | - | - |
| 80 | CS-catechol, batch 36 | 65.5 | P | - | Y | - | C, Acute In-Vivo 2 |
| 81 | CS-catechol, batch 37 | | P | - | - | - | A, Acute In-Vivo 2 |
| 82 | CS-catechol, batch 38 | | P | - | - | - | - |
| 83 | 70/30 CS-catechol, batch 39/CS | 168 | P | Y | Y | 6 mo-hs | B, Acute In-Vivo 2 |
| 84 | CS-catechol, batch 40 | 168 | P | Y | - | 6 mo-hs | C, Chronic In-Vivo |
| 85 | CS-catechol, batch 41 | - | P | Y | - | - | - |

FIG. 15E

CHITOSAN DRESSING FOR CONTROL OF BLEEDING IN TRANSURETHRAL PROSTATECTOMY

GOVERNMENT LICENSE RIGHTS

This invention was made with Government support under R42DK078400 awarded by National Institute of Diabetes and Digestive and Kidney Disease. The Government has certain right in the invention.

BACKGROUND

Technical Field

This disclosure relates to the field of chitosan materials comprising catechol modified chitosan and uses thereof.

Description of the Related Art

Current bleeding control in and after transurethral resection of the prostate (TURP) relies on cautery for small vessel arterial bleeding and application of balloon pressure to address venous oozing. The bladder neck and prostrate are both highly vascularized tissue that often continue to bleed following injury and through wound healing. The initial injury site may continue to bleed for days unless standard hemostasis is applied and the bleeding may also recur around week one or week two after TURP procedure when the scab of prostatic cavity sheds off. Current standard initial hemostasis for treatment of bleeding following TURP is to apply manual traction with a balloon catheter followed by continuous bladder irrigation with saline. Typically, balloon pressure can be applied for up to 24 hours in the case of protracted bleeding. If the bleeding is uncontrollable after the period of conservational management, the patient may have to return to surgical unit promptly to stop the hemorrhaging with either open or endoscopic procedures.

Although there have been advances in bleeding control using advanced dressings for applications outside of TURP bleeding control, none of these advances have yet translated to the unique conditions of the bladder and the prostrate where delivery, adhesion, continuous oozing bleeding and urine considerations are highly challenging. Rapid bleeding control in TURP, in open prostatectomy and in bladder resection is highly desirable.

Benign Prostatic hyperplasia (BPH) and prostate cancer are two of the most common urologic diseases that are treated with surgical intervention in aging men. An estimated 50% of men have histologic evidence of BPH by age 50 years and 75% are thought to display such evidence by age 80 years. In 40-50% of these patients, BPH becomes clinically significant. Although the incidence of uncontrolled bleeding from surgical intervention involving prostate and urethra is relatively low, it remains a significant risk that must be addressed by in hospital with a length of stay over at least two to three nights. According to statistical analysis of U.S. Department of Health and Human Service from 2005 to 2010, there was an average of 150,000 discharges from either open or transurethral procedure prostatectomy in the U.S., with direct surgery cost surpassing an average $4.5 billion annually. In these patients, the average length of hospital stay with open or transurethral prostatectomy was 3.1 and 2.4 days respectively. In the patients who had blood transfusion due to significant blood loss (4-5%) in the surgery, the average length of stay was prolonged to five or six days that cost an average $15,700 more in each case compared to the average cost ($29,300) of prostatectomy patients in 2010. The costs of the prostatectomy procedure are high because of operating-room time, surgeon time, and hospital length of stay.

TURP is considered the benchmark therapy for BPH. Partial removal (resection) of the prostate is accomplished in TURP by minimally invasive surgery through the urethra using a cystoscope (endoscope for the bladder via the urethra) and electrocautery. The thin loop electrocautery used in TURP results in less tissue necrosis than other less common minimally invasive prostatectomy procedures, however there is more intraoperative bleeding with TURP. Appropriate prostate resection and control of bleeding in TURP, like other forms of prostatectomy, are its essential challenges. The volume of the intraoperative bleeding in prostatectomy depends on the size of the prostate, the length of time to resect the prostate, and the surgeon's skill. Significant bleeding or hemorrhage after prostatectomy often causes undesirable clot retention (and resulting urinary retention) in the bladder and urethra that may prolong time in hospital, and even necessitate re-operation. In general, arterial bleeding is easily identified and controlled by electrocoagulation, but the venous bleeding common in TURP is more difficult to control. Attempts to control venous bleeding by electrocautery and irrigation may result in undesirable outcomes such as TURP syndrome. In standard of care control, venous bleeding is controlled by filling the bladder with irrigating fluid and application of an inflated transurethral balloon catheter to compress the bleeding prostatic cavity. TURP associated post-operative morbidity rate has been reported as high as 18% with an operative mortality rate of 0.3%. In older patients, the risk of blood loss related morbidity and mortality increases significantly in association with coagulation disorders and cardiovascular abnormalities. Uncontrolled bleeding during TURP is still one of the major complications of prostate resection and this often leads to converting to less desirable open surgery. Although there is significant progress in the management of BPH, the incidence of uncontrolled strong bleeding remains around 6% and blood transfusion rate to address this bleeding is 4% to 5%.

In the typical TURP, the length of hospital stay is two to four days and the patient has an inflated urinary balloon catheter in place until bleeding stops and urine becomes clear. Any significant reduction of post-op bleeding following TURP will shorten time of catheterization and hospital bed requirements. It will also decrease the incidence of urinary tract infection, catheter-related patient discomfort and related complications. Significant hematuria (blood in urine), resulting from either transurethral or open surgery, which causes hemodynamic instability and clot retention, requires immediate medical attention and medical care for hemostasis, clot clearance, blood transfusion, and coagulation evaluation. Treatment of significant hematuria through a transurethral approach is troublesome due to limited operative visual and spatial restriction. Most often the patient has to return to the operating room to perform an open bladder surgery to achieve hemostasis and remove cystic clots. A complicating factor of prostatectomy is that TURP patients are commonly anti-coagulated due to the presence of other chronic conditions such as cardiovascular disease. Although it is preferable to have these patients taken off their anti-coagulation medication such as Coumadin and Plavix before TURP surgery because of risk of bleeding, it would be preferable to be able to perform the procedure while the patient remains on their medication to reduce the possibility of stroke or myocardial infarction during the procedure. A reliable and sustainable hemostatic technique, preferably effective in the case of anti-coagulated individuals, is urgently required for the transurethral application to control significant bleeding following prostate resection.

BRIEF SUMMARY

The subject chitosan endoluminal hemostatic dressing (CEHD) of the invention provides for rapid bleeding control in the presence or absence of anticoagulants, and allows for enhanced rate of healing in the lower urinary tract from bladder neck to urethra following transurethral resection of the prostate. The subject CEHD of the invention is the first dressing to demonstrate uniform endoluminal tissue attachment with patency and control of bleeding in the urethra with promotion of healing and non-surgical removal within 7 days. The subject CEHD of the invention provides for timely CEHD deployment with significantly reduced incidence of uncontrolled hemorrhage during the resection procedure and significantly reduced clinical catheter in-dwelling time from present standard of care average two days to ≤one day of observation. The subject CEHD of the invention enables reduction in the length of hospital stay from the current standard of care three days to ≤one day realizing substantial savings in per patient healthcare cost.

The subject chitosan endoluminal hemostatic dressing (CEHD) of the invention is amenable to use in all prostatectomies including transurethral resection of the prostate (TURP).

BRIEF DESCRIPTION OF THE SEVERAL VIEWS OF THE DRAWINGS

FIG. 1E shows a preferred double balloon delivery catheter of the invention with inflated distal balloon located inside a partially filled bladder with inflation of distal balloon rupturing the protective sheath distally and along the distal seam of the sheath allowing the sheath to be removed intact by pulling on its distal end. FIG. 1F shows the double balloon catheter of FIG. 1E with the sheath fully removed and the furled dressing beneath revealed. The catheter is pulled gently from its proximal end to position the distal balloon against the bladder neck to provide for correct alignment of the more proximal balloon (not shown) and the furled dressing (shown) against the resected prostatic fossa (shown in relief). FIG. 1G shows the double balloon catheter of FIGS. 1E & 1F with the unsheathed and well located proximal balloon inflated to apply and adhere the now unfurled dressing of the invention intimately against the resected prostatic fossa.

FIG. 3a is a side-on view and FIG. 3b is a plan view.

FIGS. 14A-14G show tables of various parameters for batches used to prepare chitosan dressings.

FIG. 15A-15E show a table of various chitosan dressing preparations, including formulations, and dissolution, foldability, burst testing, ex-vivo, accelerated stability, and in vivo characteristics.

DETAILED DESCRIPTION

Figure 1A:
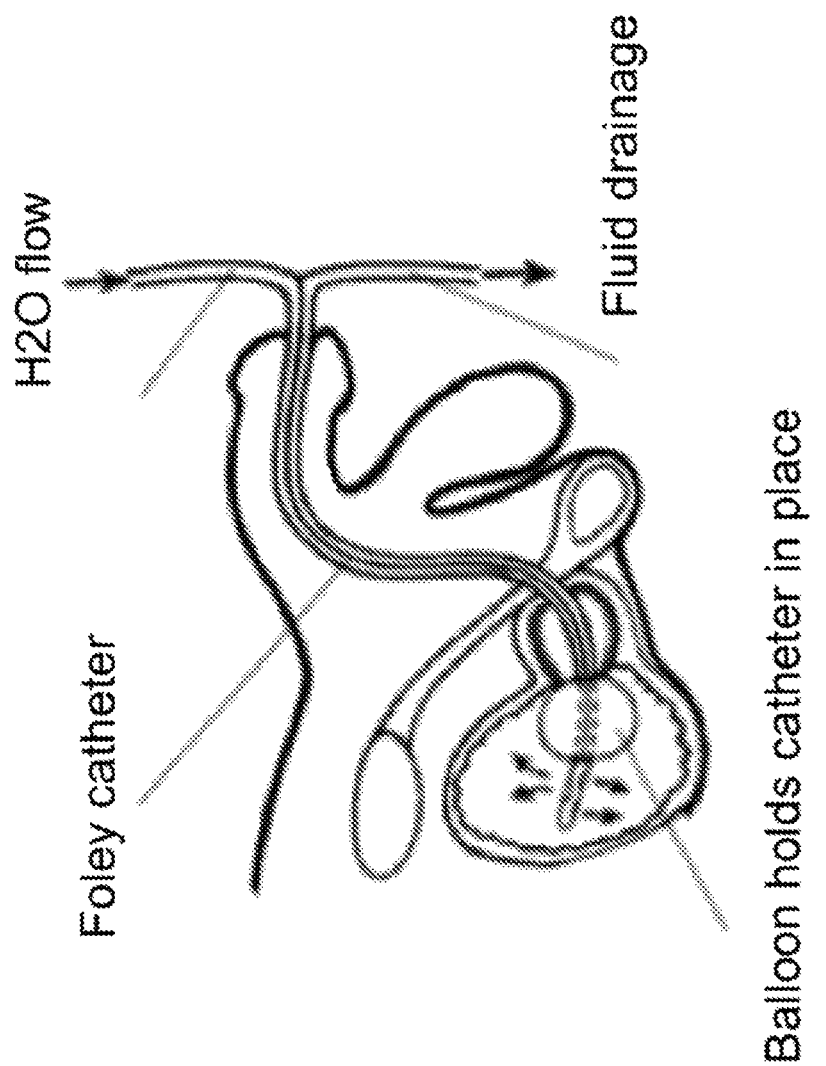
FIGS. 1A, 1B, 1C, 1D, 1E, 1F, and 1G depict the introduction, placement, and use of dressings of the present invention.
Figure 1B:
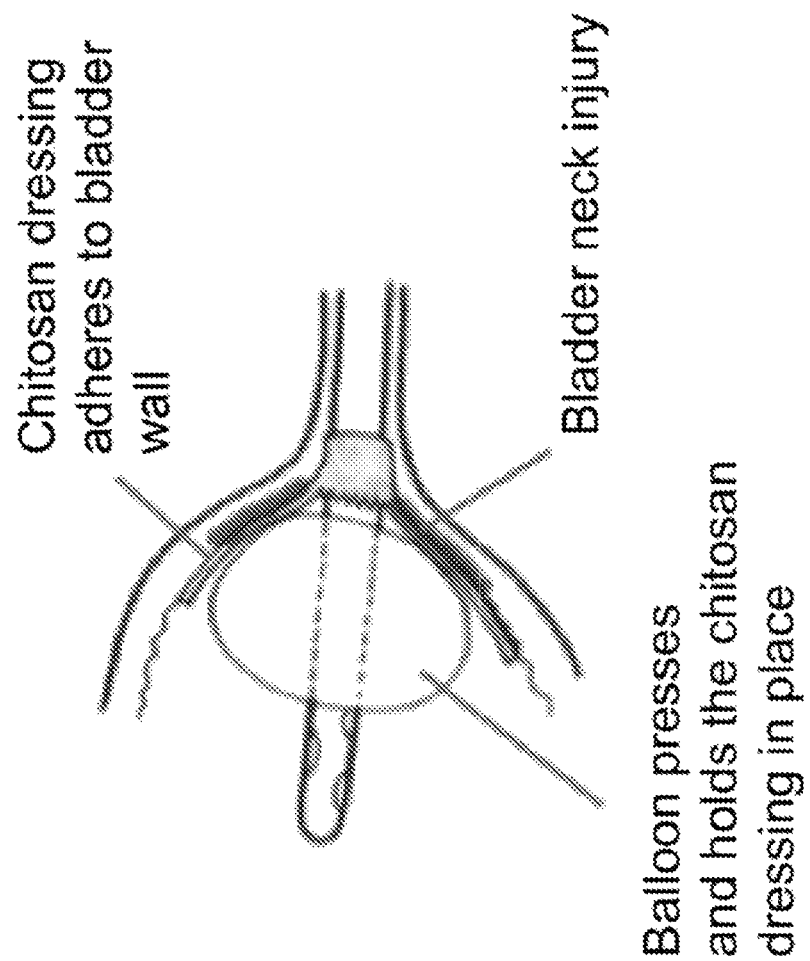
Figure 1C:
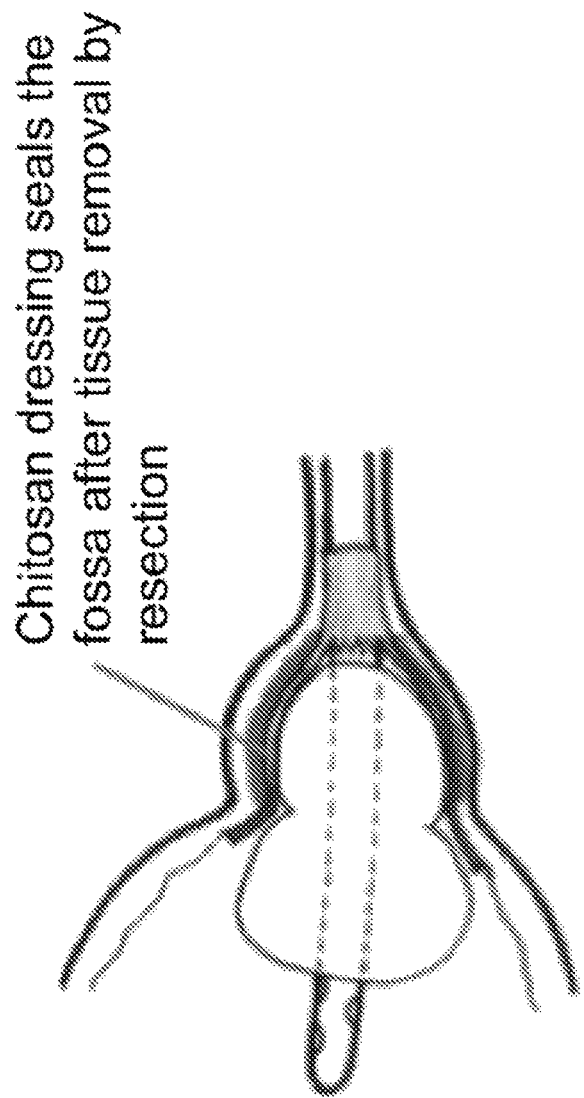
Figure 1D:
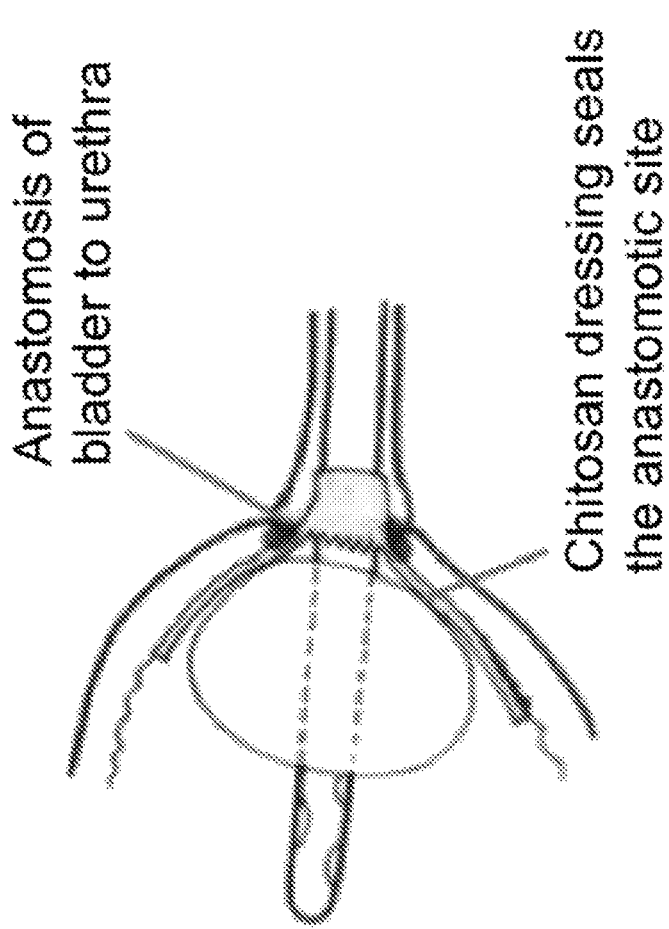
Figure 1E:
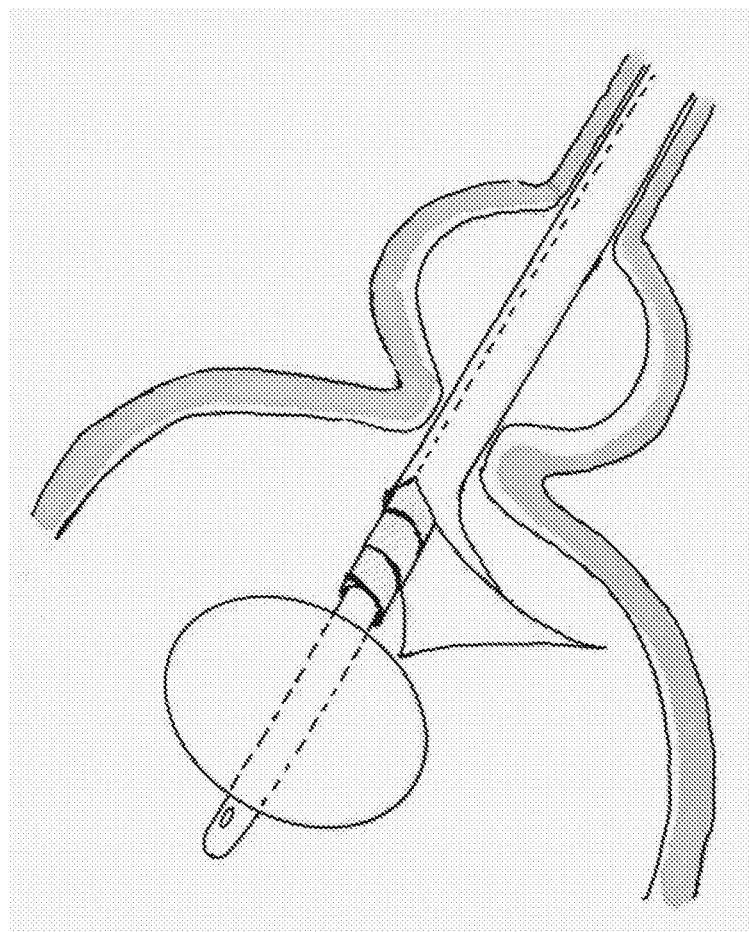
Figure 1F:
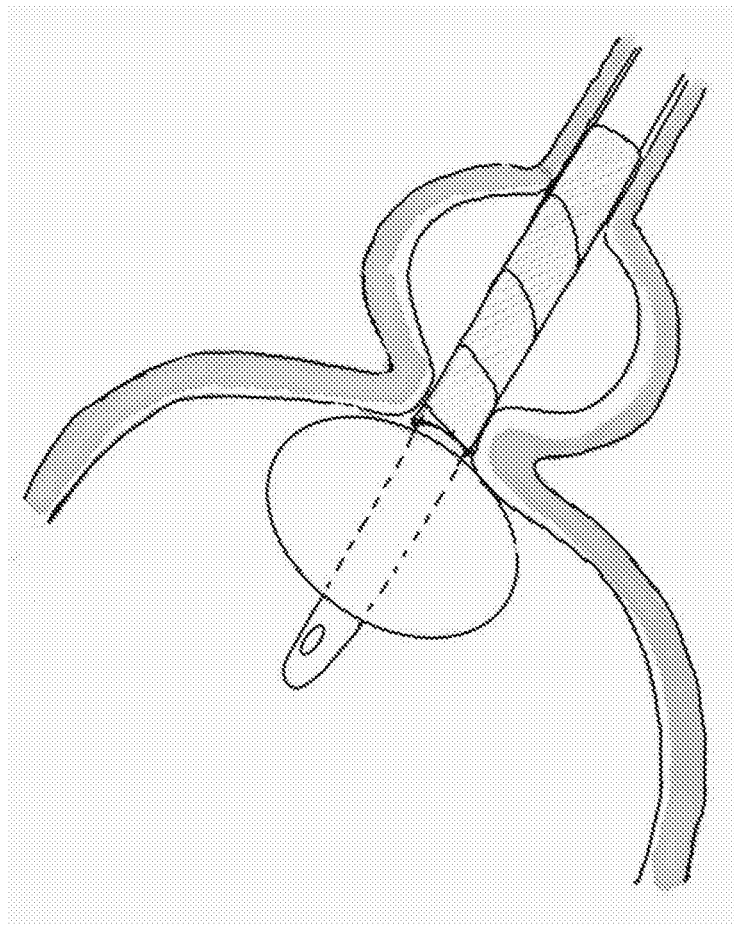
Figure 1G:
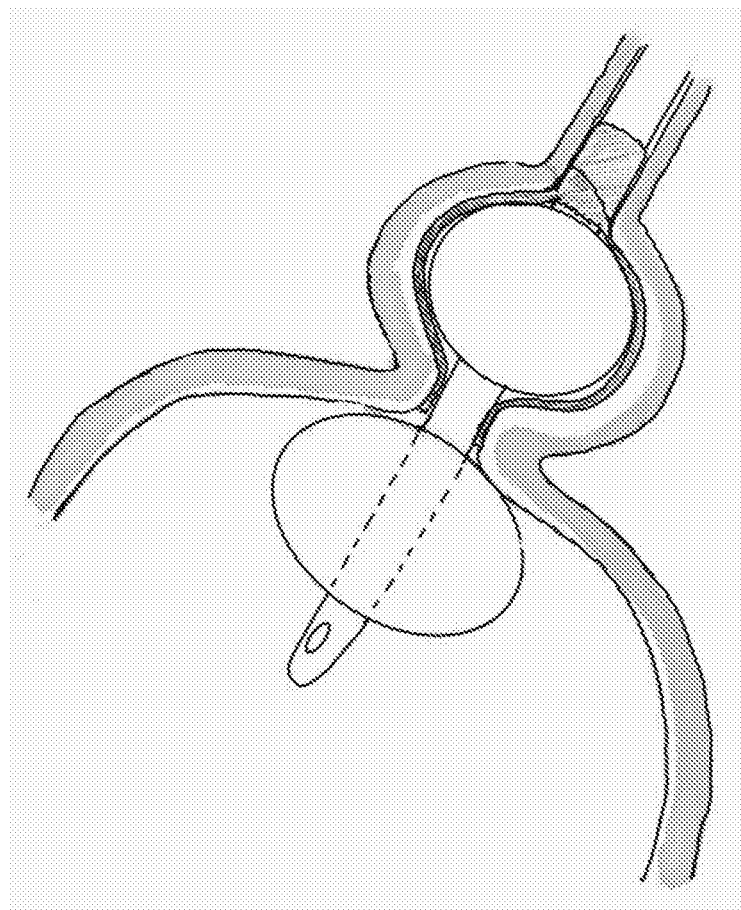
Figure 2:
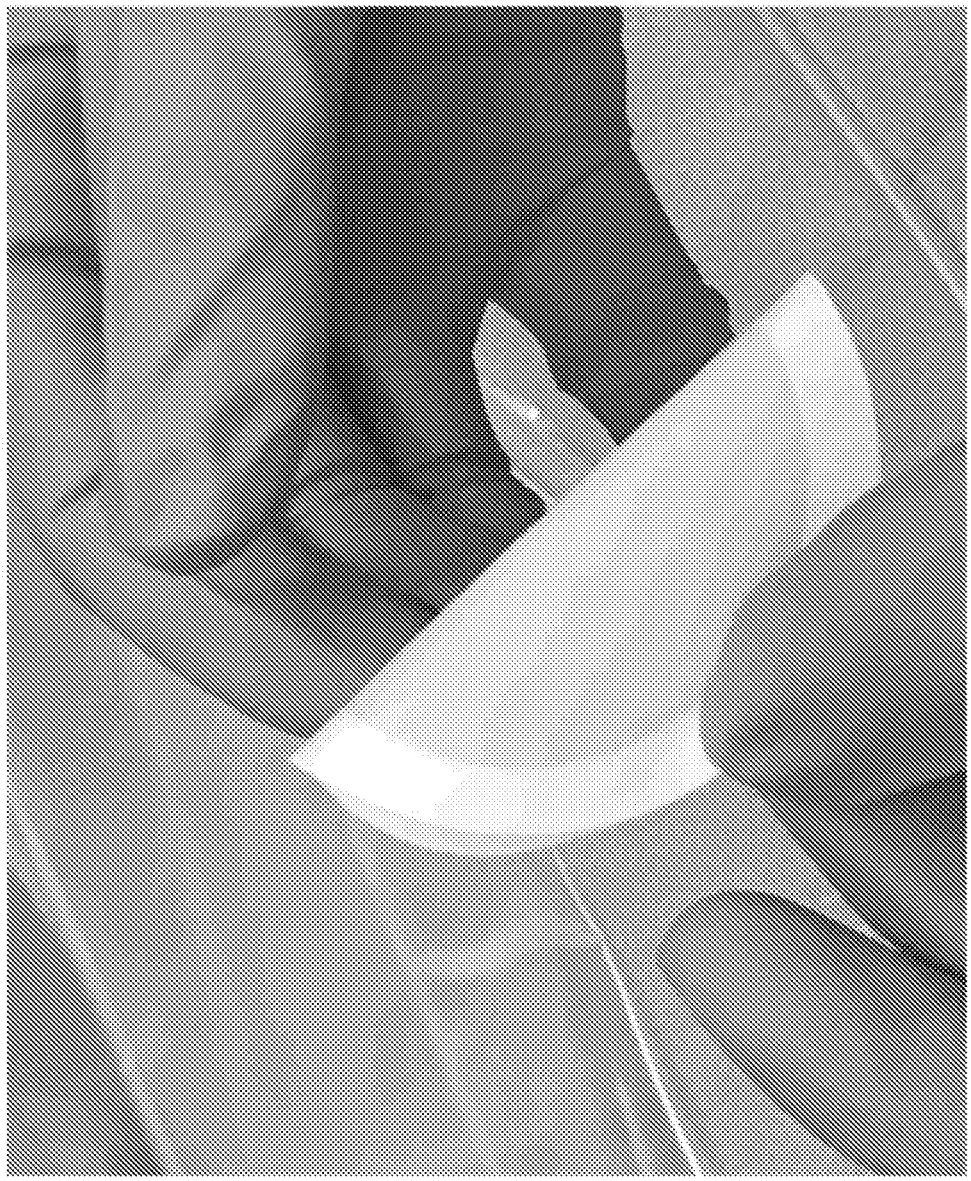
FIG. 2 depicts a digital image of gloved hands holding folded two-sided dressing of the invention with darker side being the tissue adhesive catechol modified chitosan side and the lighter side and other edge area being the unmodified chitosan dressing side (the unmodified dressing surface diameter is 2.5 inches while the modified catechol dressing surface diameter is 2 inches).
Figure 3A:
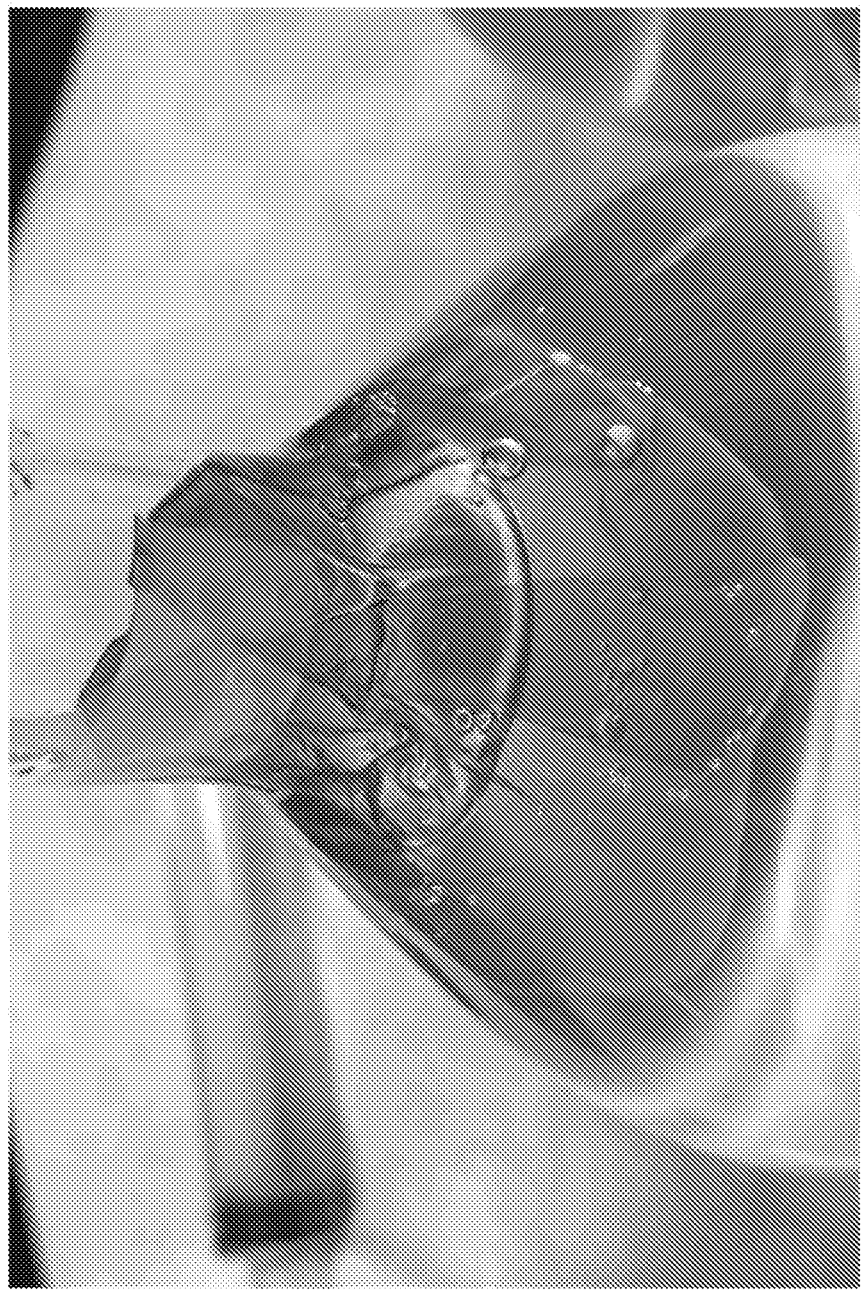
FIG. 3a and FIG. 3b depict digital images of the two-sided catechol modified chitosan dressing of the invention adhered to the wall of a 250 ml volumetric cylinder by balloon catheter application for 2 hours submerged in 0.9% w/w physiological aqueous saline solution at 25±3° C. at close to 48 hours after initial attachment. Note that there is no trace of the original unmodified chitosan dressing at 48 hours.
Figure 3B:
Figure 4:
FIG. 4 depicts a digital endoscopic image of the catechol chitosan dressing of the invention within 30 minutes attached uniformly to the bladder neck and lumen of urethra of a close to 100 lbs female swine. The bladder is swollen by urine and saline injected to aid in the viewing. The image was taken by trocar delivery of an endoscope through the wall of the swine bladder and with the endoscope viewport directed at the swine bladder neck and entrance to the urethra. The image demonstrates a patent urethra, a wispy rapidly degrading non-modified chitosan backing, and a modified catechol dressing intimately adhered to the bladder neck and lumen of urethra.
Figure 5A:
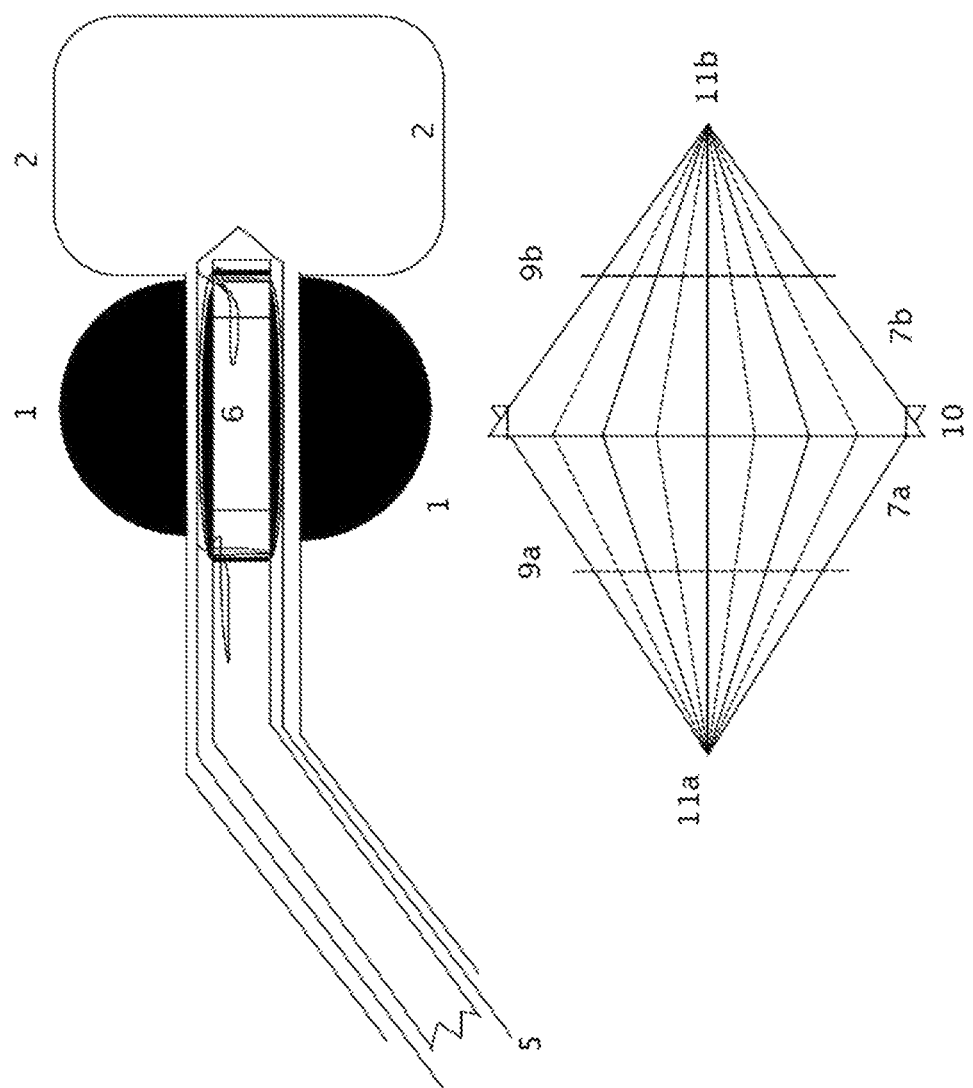
FIGS. 5A and 5B depict one image plan-view of the folded dressing all other images are cross-sectional/side on. Reference numbers, if included in the attached Figure, correspond to written text as follows: 1—Prostate; 2—Bladder; 3—Urethra mucosa; 4—Catheter body tubing; 5—Sheath; 6—Furled CEHD on delivery balloon of delivery catheter; 7a—conical folded CEHD with attachment point (14) proximal (left of) to delivery balloon catheter; 7b—conical folded CEHD with attachment point (14) distal (right of) to delivery balloon catheter; 7c—plan view of CEHD conical folded CEHD with attachment point (14) distal. Note that there may be two dressings on one balloon with distal and proximal attachments or just one dressing with proximal attachment only. An alternate delivery is with the CEHD furled as a cylinder around the delivery balloon however this is not drawn; 8—Delivery balloon (there are drawings of single balloon catheter—less preferred—and double balloon—preferred). In the double balloon catheter the delivery balloon is also the proximal balloon; 9—Cutting for creating the circular window attachment point towards the apex of the conically folded dressing (9a proximal; 9b distal); 10—Overlaying edges of two faces of conical dressings facing each other; 11—Apices of conical folded CEHD's (11a proximal; 11b distal); 12—Irrigation ports (12a proximal; 12b distal); 14—Conical folded CEHD apex attachment point to balloon catheter with body of CEHD folded over and furled around delivery balloon. A simple double sided pressure adhesive works well to attach the CEHD apex to the catheter. This attachment assists sliding the close-fitting sheath over the folded and furled CEHD without the CEHD being caught by the sheath in its application; 15—Distal or placement/positioning balloon in a double balloon delivery catheter. This is preferred over the single balloon catheter as the distal balloon can be used to rupture and initiate removal of the sheath and it provides ideal ability to locate the delivery balloon. The distal balloon may be used to achieve apposition of the CEHD against the bladder neck in the case of anastomoses and bladder neck injury; and 16—Ports for the balloon catheter (3 ports are typical in a 2 balloon catheter however a multi-lumen catheter with 2 balloons may have more). There is typically one port for each balloon and at least one point for irrigation and drainage. The ports typically connect to standard syringe luer connectors.
Figure 5B:
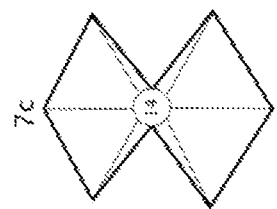
Figure 5B:
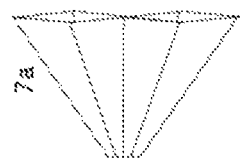
Figure 5B:
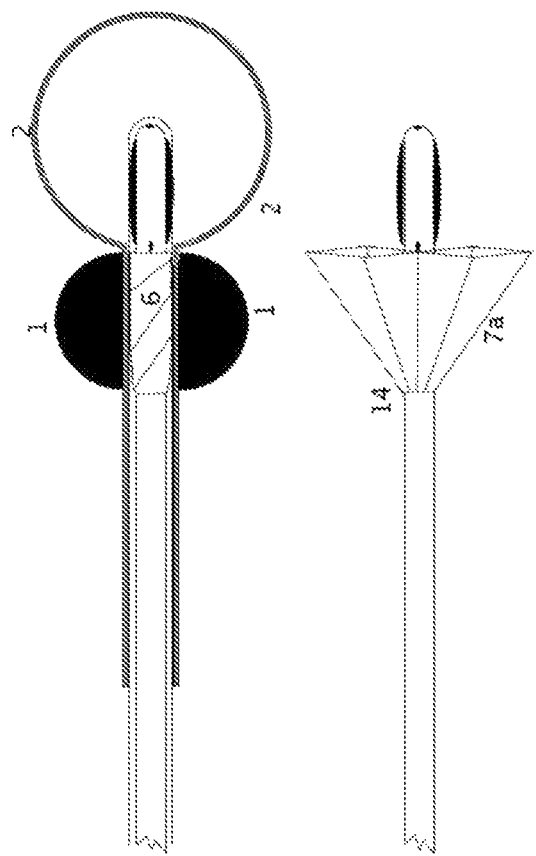

The present invention addresses rapid bleeding control in transurethral prostatectomy, open prostatectomy, bladder resection using a foldable, thin (thickness≤about 500 microns), tissue adherent, chitosan-based, hemostatic dressing. The dressing of the invention has one or more, or all, of the following features, such that it is: (1) able to be folded or furled and unfolded and unfurled without tearing or compromised mechanical performance; (2) able to be applied in the presence of blood and urine at about 37° C. without significant dimensional changes in length, width and height or loss in mechanical properties; (3) able to be delivered in the presence of urine and blood; (4) able to be delivered to injury site by a transluminal or transurethral delivery device; (5) able to be unfolded or unfurled at delivery site; (6) characterized by capillarity, porosity and absorbency that is able to remove hydrophilic and hydrophobic biological fluids that can interfere with adhesion; (7) activated by wetting to adhere to bladder mucosa, resected bladder mucosa and resected prostate on application of uniform pressure; (8) able to contact itself and packaging materials when dry without adherence to itself or to packaging; (9) inclusive of a tissue adherent side of dressing that is able to contact itself and packaging or delivery materials when wet with urine or blood without adherence to itself or to packaging or delivery materials if wet contact is not more than about 300 seconds, (10) able to uniformly adhere to tissue and quickly stanch moderate to oozing bleeding at pressure≤about 50 mmHg or, for example, a bleeding rate of between about 20 ml/min to about 100 ml/min or greater, providing opportunity to allow TURP to be performed as an outpatient procedure; (11) able to be released from the delivery device to allow withdrawal of the delivery device from the urethra; (12) able to resist dissolution on exposure to urine at about pH 4.5 to about pH 8 at about 37° C. in about the first 12 hours of application; (13) enables (with or without delivery device in place) the urethra to remain patent with dressing or residues of dressing present and allows unobstructed passage of urine; (14) protects the injury site and provides for promotion of healing; (15) provides a controlled, slow degradation and/or dissolution from the attachment site (bladder neck, prostate, and/or urethra) to allow for removal without surgical assistance in less than about 7 days.

The current invention provides: (1) an ability to rapidly control hemorrhage in prostatectomy using a noninvasive procedure; (2) an ability to control bleeding in anti-coagulated patients; (3) significantly reduced patient pain and discomfort by control of bleeding without need for prolonged catheterization; (4) significantly reduced hospital length of stay; (5) significantly reduced healthcare cost; (6) significantly reduced rate of morbidity; and (7) trending outcomes to a reduced rate of mortality.

As used herein, bladder mucosa is broadly defined to include any exposed tissue surface in the bladder including any tissue surface exposed by way of an operation (e.g. surgical operation). Bladder mucosa therefore includes bladder mucosa naturally present in the bladder, resected bladder mucosa, and resected prostate, etc.

Chitosan endoluminal hemostatic dressing (CEHD), as used herein, refers to a chitosan dressing that is hemostatic, and can be used in an endoluminal area e.g. inside bladder. CEHD is not limited by the position of its application and include chitosan dressing that is applied at any location inside a human body, including but not limited to bladder mucosa.

Bleed rates, or blood flow rates, in ml/min suitable for treatment by the devices described herein may range from about 1 ml/min to about 200 ml/min. In preferred embodiments, the bleeding rates addressed by the devices range from about 1 ml/min to about 150 ml/min. A bleed rate of between about 20 ml/min and 25 ml/min is considered "brisk" bleeding. Oozing bleeding is generally greater than about 1 ml/min as it is noted that low bleeding rates such as 1 ml/min typically clot and stop of their own accord unless the subject is on anticoagulation therapy or has a disorder of the clotting cascade due to reasons other than taking anticoagulation medication. For such a subject with irreversible anticoagulation medication or with a bleeding disorder, 1 ml/min oozing bleeding remains concerning and needs to be addressed such as by the device of the invention. In some embodiments, the devices described herein are used to address TURP bleeding rates of between about 1 ml/min and about 25 ml/min, or about 1 ml/min and about 20 ml/min, or about 1 ml/min and about 15 ml/min, or about 1 ml/min and about 10 ml/min, or about 1 ml/min and about 5 ml/min.

A TURP delivery device may include any device that is used in a TURP procedure or any device used in connected with a TURP procedure.

Chitosan Dressing

Chitosan dressings may refer to compositions that include varying amounts of chitosan. The general contents, general chemical compositions and different forms of a chitosan dressing are described, for example, in U.S. Pat. Nos. 7,820,872, 7,482,503, 7,371,403, 8,313,474, 7,897,832, 9,004,918, 8,920,514, 9,204,957, 8,741,335, 8,269,058, 9,205,170, and 10,086,105. Such chitosan dressings, due to their chemical and physical properties as described previously, have been used to stop bleeding.

The chitosan used preferably comprises the non-mammalian material poly[.beta.-(1.fwdarw.4)-2-amino-2-deoxy-D-glucopyranose. The chitosan can be processed in conventional ways from chitin obtained, for example, from animal crustacean shells such as shrimp. Chitosan may be biocompatible and biodegradable within the body, and is capable of being broken down into glucosamine, a benign material. The catechol-modified chitosan used herein may include reference to catechol-added chitosan.

A chitosan dressing can be dry or wet. A chitosan dressing is "dry" if the moisture content in the chitosan dressing is less than about 15% by weight, preferably about 10% by weight, and more preferably about 5% by weight. A chitosan dressing is "wet" when the chitosan dressing has come in contact with a source of water, including water in a physiological environments and biological fluids, or in an aqueous solution. For example, a chitosan dressing becomes wet when the chitosan dressing, as described in this disclosure, comes in contact with urine or blood or a bladder tissue surface (bladder mucosa). The chitosan dressing, remaining substantially in a solid form absorbs, displaces, redirects or channels water/moisture in the physiological environment of bladder mucosa in amounts sufficient to permit adhesion of the chitosan dressing to the tissue surface. The adhered chitosan dressing can be used to seal wound surfaces and slow or stop further bleeding.

In a preferred embodiment, the chitosan endoluminal hemostatic dressing (CEHD) of the invention contains preferably greater than or equal to 25% by weight chitosan; more preferably greater than or equal to 50% by weight chitosan and most preferably greater than or equal to 75% by weight chitosan. Chitosan is a generic term used to describe linear polysaccharides that are composed of glucosamine and N-acetyl glucosamine residues joined by β-(1-4) glycosidic linkages (typically the number of glucosamines≥N-acetyl glucosamines) and whose composition is soluble in dilute aqueous acid (Roberts 1991). The chitosan family encompasses poly-β-(1-4)-N-acetyl-glucosamine and poly-β-(1-4)-N-glucosamine with the acetyl residue fraction and its motif decoration (either random or block) affecting chitosan chemistry. The C-2 amino group on the glucosamine ring in chitosan allows for protonation, and hence solubilization of chitosan in water (pKa≈6.5) (Roberts 1991). Other hydrophilic polymers such as, for example, guar, pectin, starch and polyacrylic acid may be used.

In a preferred embodiment, the dressing of the invention is polymeric, thin (preferably dry dressing thickness of about ≤500 microns, more preferably thickness of about ≤200 microns or about ≤100 microns, most preferably thickness of about ≤150 microns), flexible, porous, dry, biocompatible, tissue adherent and hemostatic. In some embodiments, the dressings are about 100 microns in thickness, and may comprise a bilayer dressing of two about 70 micron layers (one layer that is adhesive and resistant to dissolution and one layer that is straight chitosan) with sum thickness nearer 150 microns on delivery.

The dressings are not limited in shape, however square, rectangular, circular, or circular petal shaped dressings are preferred. In one embodiment, a maximum size could be up to about 50 mm×50 mm square or 50 mm in diameter. In another embodiment, dressing size could be about 45 mm×45 mm square or 45 mm in diameter, 40 mm×40 mm square or 40 mm in diameter, 35 mm×35 mm square or 35 mm in diameter, 30 mm×30 mm square or 30 mm in diameter, 25 mm×25 mm square or 25 mm in diameter, 15 mm×15 mm square or 15 mm in diameter, 10 mm×10 mm square or 10 mm in diameter, etc. In still another embodiment, each of the length and width may range from about 10 mm to about 50 mm, or from about 10 mm to about 50 mm in diameter. As dressings become larger in size they become increasingly subject to delivery limitations in confined cavities.

In another preferred embodiment, the dressing is delivered by balloon catheter, and the dressing has a diameter size of about around 5 cm, or 7 cm maximum. The balloon catheter is preferably passed through a central small hole (about same diameter as catheter balloon which is generally about 4 mm to about 7 mm diameter, or the hole can be larger, e.g., up to 12 mm) in the dressing and the dressing (dressing 30 mm to 70 mm diameter) is adhered to the catheter tubing (same diameter as catheter) opposite the balloon by small dressing tabs either side of the hole. In some embodiments, the surface area change in the dressing from a folded, furled, or compacted condition is about ⅛ of the surface area when the dressing is in an unfolding, unfurled, or uncompacted condition. Dressings described herein may provide a large dressing surface area in an open, unfurled, or unfolded condition. Alternatively, dressings described herein may provide a small dressing surface are in a closed, furled, or folded condition. The ability of the dressings to be folded, furled, or closed allows them to be more compact and protected for delivery and reduces the likelihood that the dressing surface is prematurely wetted prior to delivery to a target tissue treatment site.

In a preferred embodiment, the dressing is about 100 microns thick, is about 5.0 cm in diameter, and will have an open, unfurled, or unfolded outward facing surface area of about 38.66 $cm^2$. On the balloon delivery device, a closed, furled, or folded dressing will have an outward-facing cylindrical surface area (in a 2.5 cm long cylinder) of about 5.09 $cm^2$ on a 7 mm diameter catheter balloon, or about 14.0 $cm^2$ open and 1.85 $cm^2$ closed on a 4 mm diameter catheter balloon with a 3.0 cm diameter dressing. Thus, in one example, a dressing of the present invention may, in an open, unfurled, or unfolded condition, have an outward facing surface area that is about eight (8) times greater than the outward facing surface area of that same dressing when it is in a closed, furled, or folded condition. In some embodiments, the ratio of the outward facing surface area of an open, unfurled, or unfolded to a closed, furled, or folded dressing is about 15:1, or about 14:1, or about 13:1, or about 12:1, or about 11:1, or about 10:1, or about 9:1, or about 8:1, or about 7:1, or about 6:1, or about 5:1, or about 4:1, or about 3:1, or about 2:1.

It is noted that the most common catheter balloon used with a delivery device in TURP is 0.4 cm diameter (4.0 mm) and hence this is the most preferred size for the dressing delivery. Alternatively, a more preferred size is 0.5 cm diameter, which is a standard catheter diameter for a TURP delivery device but less common than the 0.4 cm catheter. Another preferred catheter diameter size of a TURP delivery device is between 0.5 cm and 0.7 cm which is more a custom channel size and, thus, less common than the 0.4 or the 0.5 cm catheter diameter size.

A dressing as described herein is able to be folded and unfolded, is not readily soluble in blood or body fluid, such as urine, at about 37° C. within, preferably, the first 6 hours of application, more preferably the first 12 hours of application, and most preferably the first 24 hours of application, and degrades and/or dissolves fully in contact with bladder fluids at about 37° C. within about 7 days.

A dressing as described herein will not adhere to the delivery device, and does not swell or shrink appreciably, i.e., it does not increase or decrease in size by more than about 25% in length and width, or more than about 50% in thickness, in the presence of blood and urine at about 37° C.

In a preferred embodiment, the dressing may be terminally sterilized without affecting dressing characteristics. When it is stored under controlled conditions in its packaging at room temperature of about 21° C. to about 25° C., its tissue adhesion properties, mechanical properties, dissolution properties in bladder fluids, swelling properties, and hemostatic properties are stable and do not change appreciably over time (e.g., about ≤2 years).

A preferred embodiment, the dressing has a tissue adhesive side and a non-adhesive side. In this embodiment, the non-adhesive side may provide a surface that when wet readily slides away from itself and from any applicator or delivery device surface that is applying pressure against the dressing inside a lumen, and/or in the bladder.

A preferred embodiment of the dressing is that it is formed of a substantially dry chitosan composition with a water content of about ≤15%, or about ≤8%. The dry chitosan composition is preferably formed using phase separation and drying of an aqueous solution of chitosan and water. The dry chitosan dressing is preferably prepared in sheet form which may be cut to size.

Preferred embodiments of the biocompatible, bio-dissolvable, tissue adherent chitosan dressing are able to resist dissolution in bladder fluid and blood at about 37° C. for at least about 6 hours is tissue adherent and includes materials and material structures that promote resistance to rapid dissolution and degradation in urine of the bladder. This is a significant advantage of the chitosan dressings disclosed herein.

Chitosan dressings provided herein can be applied to a mucus surface, e.g., in the bladder by light pressure, or pressure of up to hundreds of KPa. Light pressure applied to the dressing on a tissue surface as used herein indicates a pressure that attaches and keeps a chitosan dressing in contact with an injury site without significant deflection or movement of the tissue so as to allow the chitosan dressing, through its compositional structures and characteristics, to interact to promote adherence with the injury site to stop bleeding. In some embodiments, a light pressure is a pressure at about most preferably 10 kPa or less, more preferably 25 kPa or less, or preferably 50 kPa or less (note 100 g/cm2=9.8 kPa). In TURP, pressure can be applied for, typically, 3 mins to 180 mins since the balloon can be pressurized and left in place.

Production of Chitosan Dressing

The chitosan dressings of the present invention may be generated using various methods and processes. In some embodiments, the chitosan dressing may be formed by freeze phase separation and drying. In an alternate embodiment, the dressing is formed by addition of a foaming agent to provide a low density foam before freezing followed by drying. Freeze phase separation followed by removal of frozen solvent by sublimation is called freeze drying. Freeze phase separation is a process of solidification from dilute solution whereby removal of heat and resultant lowering of temperature through a container or mold surface holding the dilute solution results in a localized solid crystal nucleation of pure solvent and subsequent propagation and growth of pure solvent crystal. A result of the pure solvent crystal growth in a dilute solution is that solute diffuses away from the growing crystal front to solidify at the interstices between the growing crystal. Freeze phase separation of dilute polymer aqueous solutions results in alternate layers of thin polymer lamella between thicker layers of ice. Removal of the ice by methods which do not disrupt the polymer lamella results in a low-density polymer dressing with inter-connected porous structure. For example, in one embodiment, low-density polymer dressings may have an initial dressing density from about 0.005 $g/cm^3$ to about 0.05 $g/cm^3$.

In an alternate embodiment, the freeze phase separated dressing is formed by freezing of a foamed dilute solution followed by drying. In an alternate embodiment, the dressing is formed by non-woven fiber spinning processes, such as centrifugal spinning, electrospinning or solvent fiber extrusion into a coagulation bath. In yet another alternate embodiment, the dry dressing of the invention may be formed from a woven fiber process. In yet another alternate embodiment, the dry dressing of the invention may be formed by phase inversion and precipitation with a non-solvent (as is typically used to produce dialysis and filter membranes). In still another alternate embodiment, the dressing of the invention may be formed from an additive 3D printing process.

In a preferred embodiment of the invention, the dressing preparation process may include a compression process that changes the initial dressing density from an initial preferred range of about 0.005 $g/cm^3$ to about 0.05 $g/cm^3$ to a final preferred range of about 0.03 $g/cm^3$ to about 0.7 $g/cm^3$; however, ranges of about 0.08 $g/cm^3$ to about 1.2 $g/cm^3$ are also contemplated. It is noted that a density of about 1.5 $g/cm^3$ is the density of void-free chitosan dressings. The compression process may include application of temperature in the range of about 20° C. to about 150° C. To avoid substantial dressing swelling of the dry compressed dressing on contact with biological fluid, the temperature of the compression is preferably applied by a method that may include but not be limited to convection, conduction and radiation, and the temperature of the compressed dressing should preferably be maintained at least about 80° C. for at least about 15 seconds.

Heat during compression is a tool that allows plasticization and molding of the chitosan without cracking or tearing of the chitosan (non-destructive molding). The first glass transition temperature (Tg) of pure dry chitosan is near 80° C. which if processed near in the case of pure dry chitosan will allow ready non-destructive molding of the chitosan as well as some crystalline annealing of its structure. It is possible to lower the Tg by application of plasticizers such as water or glycerol to the chitosan and hence provide a similar level of non-destructive molding at lower temperature. Here, it is noted that chitosan can be molded non-destructively in the range 20° C. to 150° C. Outside of this range it would still be possible to non-destructively mold the chitosan but much more difficult. Above 150° C. the chitosan begins to thermally degrade while below 20° C., the addition of plasticizers may lead to undesirable loss of chitosan crystallinity which provides for dissolution resistance and resistance to degradative processes such as occur in sterilization.

Preferably, the compression prevents substantial swelling of the dry compressed dressing on contact with biological fluid and is performed with moisture content of the dry dressing during the compression at about ≤15% w/w. The compression may be applied through twin or multi-roller compression and/or uniaxially between adjacent platens.

The compression may be against a uniform flat or curved surface to provide a smooth finish to the compressed dressing.

Alternatively, the compression may be applied against an etched, machined, ablated or other type of surface treatment that imparts a depleted or added surface texture. The surface texture may be a random or it may be a regular repeated pattern. The pattern of the surface may assist in folding and unfolding or furling and unfurling the dressing and may provide for hinge-like properties in the dressing. Such texture may be used as an adjunct to quickly lock the dressing in place and stop it moving when applied. Movement of the surface of the dressing while positioned against the target tissue surface can cause filming and hence closure of the open surface structure which can lead to loss ability to remove anti-adhesive biological fluid at the surface and hence loss of ability to adhere the dressing to the surface. The timescale of the changes occurring at the dressing surface is very important such that surface uptake of fluid with significant surface dressing channel closure is highly undesirable. A good way to avoid such movement is to physically fix the dressing in place as soon as it contacts the tissue surface.

Prior to the present invention, thin solid chitosan dressings were generally rigid, not flexible enough to be bent or folded or furled without breaking, fracturing, or otherwise losing their intact shape or becoming otherwise unsuitable for use. Chitosan dressings provided herein, due to their compositional structures and characteristics, can be folded and unfolded along a folding axis while still being intact and suitable for use in stopping bleeding. Interestingly, and contrary to expectation, it has been found that chitosan dressings described herein, when folded, become less resistant to tearing or breakage along their folded seams. In some embodiments, the chitosan dressing provided herein, due to its compositional structures and characteristics, can be furled without losing its compositional structures and characteristics and still being intact and able to stop bleeding. In some embodiments, the chitosan dressing provided herein, therefore, is able to be delivered by balloon catheter along the urethra while still maintaining their compositional structures and characteristics intact. Exemplary diameters of the balloon catheter supporting the chitosan dressing can include a diameter of about 12 mm or less, and including, but not limited to, 3 mm, 3.5 mm, 4.0 mm, 4.5 mm, 5.0 mm, 5.5 mm, 6.0 mm, 6.5 mm, 7.0 mm, 7.5 mm, 8.0 mm, 8.5 mm, 9.0 mm, 9.5 mm, 10.0 mm, 10.5 mm, 11.0 mm, 11.5 mm, and 12.0 mm.

Catechol Modified Chitosan; and its Production

The chitosan dressings described herein relate to chitosan dressings comprising catechol modified chitosan and/or hydrophilic polymers. Other aspects of chitosan dressing comprising catechol modified chitosan are described in more details below.

Preferred embodiments of the chitosan endoluminal hemostatic dressing (CEHD) of the invention include compositions with catechol modified chitosan and/or, optionally, other hydrophilic polymers. Preferably the catechol modified chitosan in the dressing provides prolonged adherence to wetted tissue with tissue adherence≥about 1 kPa resisting dissolution in water, saline solution, blood and/or bladder fluid at about 37° C. for ≥about 6 hours. Preferably the catechol modified chitosan is formed by N-acylation of the C-2 amine on the chitosan glucosamine by 3,4-dihydroxyhydrocinnamic acid (alternatively named 3-(3,4-Dihydroxyphenyl)propionic acid, Hydrocaffeic acid)). Alternatively, the chitosan N-acylation to produce a catechol modified chitosan may include but not be limited to a modification with one of a 3,4-Dihydroxycinnamic acid (caffeic acid); a trans-3,4-Dihydroxycinnamic acid (trans-caffeic acid); and a 3,4-Dihydroxyphenylacetic acid (DOPAC, Homoprotocatechuic acid).

The presence of catechol in the composition provides for some poly-conjugated structure as the catechol is oxidized to o-quinone. This causes visible difference between the unmodified chitosan and catechol modified chitosan compositions, which may be off-white or pink to dark brown in color, respectively. It is noted that the catechol modified chitosan compositions go from pink to brown when oxidation occurs in the catechol.

Pink coloration in the catechol modified chitosan, signifying substantial absence of crosslinking, is provided in the aqueous synthesis by maintaining pH reaction solution at or below pH 5.5. The pink coloration may also be provided in the aqueous synthesis by performing the modification and subsequent processing steps substantially in the absence of oxygen such as by using aqueous systems purged with an inert gas which may include but not be limited to argon or nitrogen. Although the pink coloration is not desirable in the final solution or catechol modified product, it may be desirable in intermediate handling stages (such as immediately after chitosan derivatization with catechol and/or dialysis and/or washing of the subsequent catechol chitosan solution to remove residual unreacted material) because it allows for stable dry product polymer storage and dry product weight determination with subsequent ability to substantially re-dissolve the pure dry catechol modified product in water to a desired dry weight at a later time. This water-soluble chitosan catechol material is then subsequently oxidized and crosslinked (with brown coloration). However catechol modified chitosan which is dried before oxidation is not suitable for use in the chitosan dressing of the invention because dressings including such treated catechol modified chitosan are not readily redissolved and the final solution includes an undesirable mass fraction (>5% w/w) of insoluble particulate (>10 microns in diameter). Additionally catechol chitosan prepared after an intermediate freeze drying stage is more prone to early dissolution. It is noted that too much crosslinking in TURP (i.e. brown color) is less desirable as this makes the dissolution in urine take longer, for example, longer than 168 hours when the target complete dissolution is between about 72 hours to about 168 hours).

In a preferred embodiment, the catechol modified chitosan is not removed from solution by an intermediate drying step to allow for storage but rather it is kept in aqueous solution and oxidized in aqueous solution by exposure to higher than about pH 5.5 in the presence of atmospheric oxygen. Preferred pH control is achieved by adjustment of partial pressure of aqueous dissolved carbon dioxide (increased partial pressure reduces pH while decreased partial pressure increases pH to nearer pH 7). An alternative preferred means of pH control is by incremental addition of a strong acid to lower pH and a strong base to raise pH. Examples of strong acids may include, but are not limited to, hydrochloric acid, sulphuric acid and nitric acid. Examples of strong bases may include but not be limited to sodium hydroxide and potassium hydroxide. Subsequent drying of this aqueous water-soluble oxidized catechol modified chitosan results in a preferred level of crosslinking of the catechol chitosan with good resistance to dissolution and degradation in the bladder. The catechol chitosan solution may be diluted by addition of water or concentrated by water removal. The water may be removed by the techniques including, but not limited to, ultrafiltration, reverse dialysis and centrifugation. The solid fraction of the solution may be determined by sampling a known volume from the solution and performing analyses including but not limited to gravimetry, fourier transform infrared spectroscopy, ultraviolet-visible spectroscopy, refractometry, and pycnometry.

Figure 16:
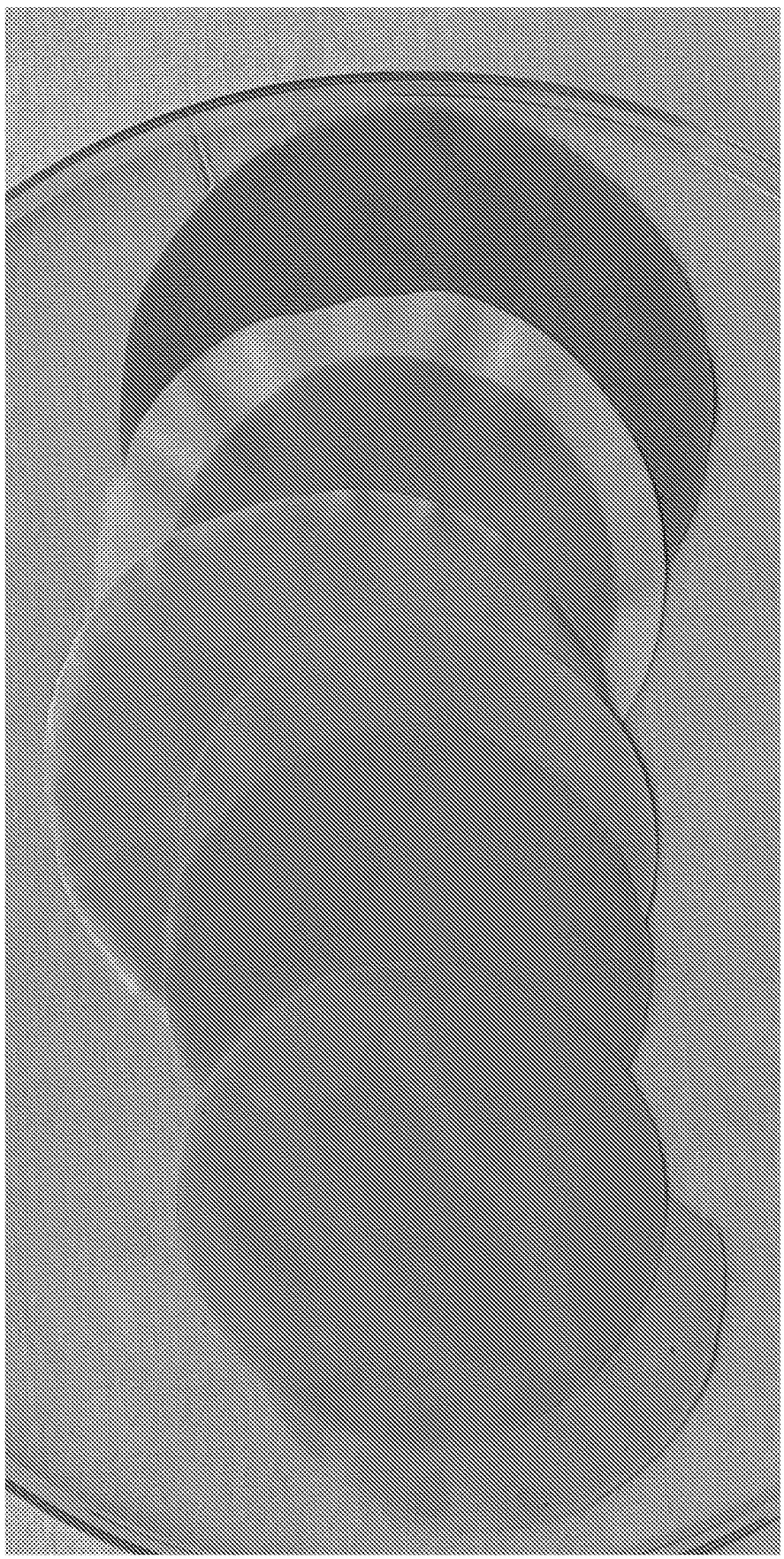
FIG. 16 depicts round-shaped catechol modified chitosan dressing that are (pre-cut) 2.5 inches by 2 inches in diameter and compressed to near 50 microns. The coloration of these catechol modified chitosan dressing, starting from left to right, ranges from light pinkish brown (first dressing), 2 dressings of darker pinkish brown, 2 tan brown colored dressings (no pink), 1 brown dressing and lastly 1 darker brown dressing. Catechol chitosan dressings 5 and 6 are formed from 2.5 inch and 2 inch molds and they are backed with unmodified chitosan dressings both from 2.5 inch molds and the unmodified chitosan can be seen clearly as the white halo (no brown or pink color) in dressing 6. The catechol chitosan and unmodified chitosan dressings were adhered together during compression to a final shared density>0.4 g/cm$^3$. The pink coloration is associated with unoxidized catechol while the brown color is associated with the oxidized catechol (o-quinone). The lighter browns and lighter pinks are associated with lower degree of substitution of the chitosan with catechol (nearer to 10%) while the darker colorations (pinkish brown and brown) are associated with higher degree of substitution of the chitosan with catechol (nearer to 20%).

In a preferred embodiment, the catechol modified chitosan composition is of a brown color resulting from catechol oxidation to o-quinone. The quinone is produced by autoxidation of the catechol hydroxyls in the presence of oxygen and at pH above about 5.5. Schiff base reaction of quinone with chitosan C-2 amine produces crosslinking in the modified chitosan. The color of the catechol modified chitosan composition is controlled during synthesis by controlling pH and oxygen exposure. Maintenance of pH at or below about pH 5.5 inhibits the production of o-quinones. Subsequent conditioning of dialysis solution, final washed, or dialysed catechol chitosan solutions in a preferred pH range 5.8 to 6.2 provides for more dissolution resistant, darker, more oxidized catechol. In some embodiments, the coloration of catechol modified chitosan characterizes one aspect of the catechol modified chitosan dressing. In some embodiments, the coloration reflects the degree of substitution of the chitosan with catechol. In some embodiments, the coloration from pink to brown correlates with the degree of substitution. FIG. 16 shows exemplary embodiments of different colorations reflecting and correlating with different degree of substitution of the chitosan with catechol.

In order to prepare a dry dressing from the catechol chitosan, a preferred light brown to darker brown catechol aqueous chitosan solution is prepared which may be used by itself or may be mixed with other aqueous hydrophilic polymer solutions including but not limited to solutions of chitosan and/or, optionally, hydrophilic polymers. Preferably, the dry phase separated catechol chitosan dressings are prepared as densified dried freeze-phase-separated and fibrous dressing structures.

Figure 6:
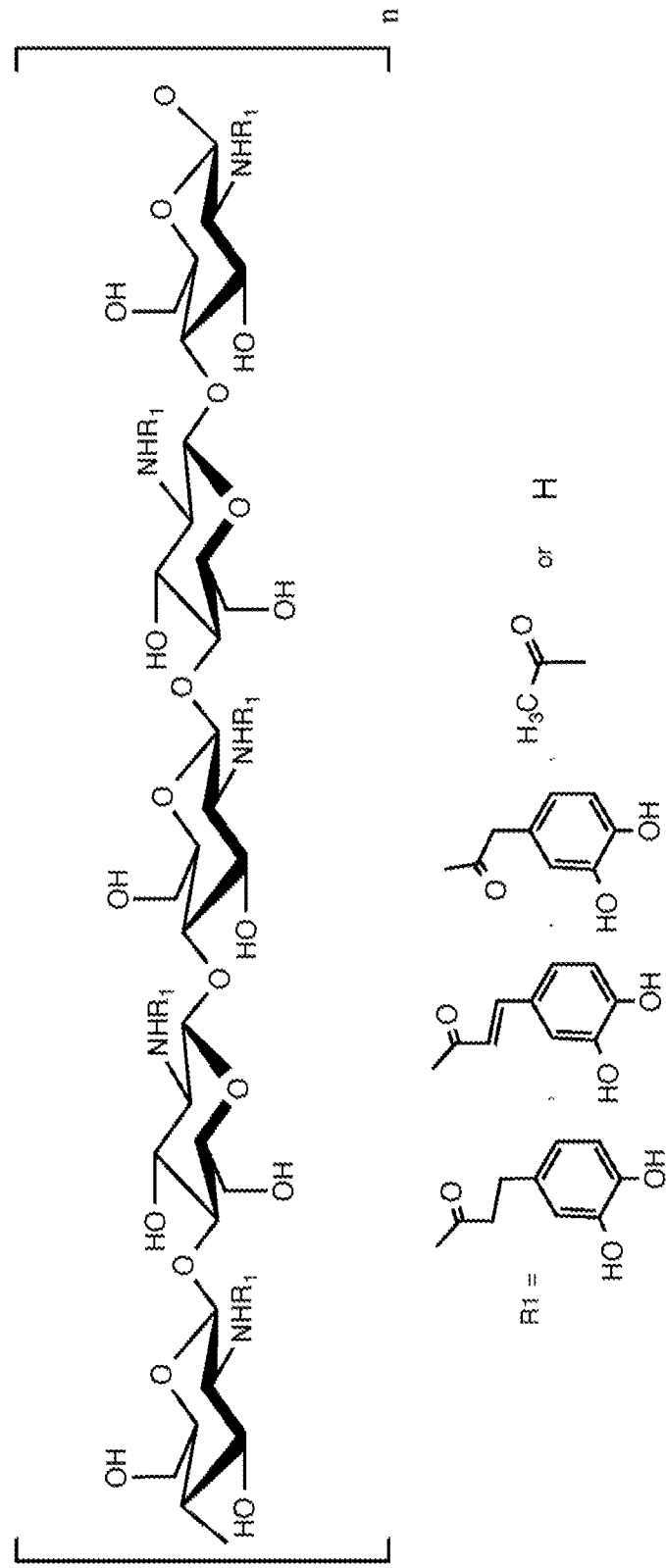
FIG. 6 depicts a chemical structure representation of chitosan (R1=H and acetyl radical) and catechol modified chitosan (R1=H, acetyl, hydrocaffeic acid radical, caffeic acid radical, trans-caffeic acid radical and Homoprotocatechuic acid radical). For chitosan polymer, preferably n>60, more preferably n>300, and most preferably n>600.

Preferred crosslinked catechol modified chitosan compositions of the invention provide good tissue adherence and 10 times to 100 times increased resistance to dissolution in the bladder compared to dressings formed substantially of unmodified chitosan. For example, FIGS. 6A, 6B, and 6C show dissolution testing results demonstrating that chitosan dressings are gone in 15 minutes while some catechol dressings lasted greater than 24 hours. The catechol modified chitosan compositions described herein, provide hitherto unknown longevity, biocompatibility, and ability to eventually dissolve.

Preferred rapid adherence to bladder mucosa of the chitosan endoluminal hemostatic dressing (CEHD) of the invention (≤1 minute) is provided in the dry chitosan dressing by the promotion of quaternary ammonium cation formation at the chitosan glucosamine C-2 amine by the presence of an acid in the dry dressing composition. Preferred chitosan acid salts in the dressing may include salts of acetic, lactic, glycolic, citric, succinic, malic, hydrochloric, glutamic, ascorbic, malonic, glutaric, adipic, pimelic, and tartaric acids, and combinations thereof. Preferably the acid salt % weight of the chitosan is greater than about 2% and less than about 15%. To achieve fast adherence (e.g., ≤1 minute) to wet tissue, the moisture in the dry bladder dressing is preferably less than about 15% by weight; more preferably it is less than about 10% by weight and most preferably it is less than about 5% by weight.

In the case of densified freeze-phase-separated and dried chitosan dressings, the chitosan solution is poured into the freeze-phase-separation mold (typically in the shape of a pan with a horizontal flat base) with preferably around a 0.1% w/w, more preferably around 0.5% w/w and most preferably 0.25% w/w hydrophilic polymer chitosan solution. The hydrophilic polymer solution is preferably added to the horizontal flat pan to a vertical depth of preferably about 10 mm, more preferably 2.5 mm and most preferably 5.0 mm mold depth. The solution in the mold is subsequently frozen and dried to remove water by sublimation or freeze phase substitution (solvent extraction of the ice with a non-solvent to the polymer) to a low density (>99% void volume) open or porous dry sponge with a dry density<about 0.01 g/cm$^3$ (or, for example, about 0.005 g/cm$^3$ for a catechol chitosan uncompressed dressing from 0.5% solution, which is about ⅕ or 20% of the density of an uncompressed HemCon Bandage chitosan sponge, which is about 0.025 g/cm$^3$). Lyophilization is typically performed at pressure below 300 mTorr while freeze substitution involving a dry, cold (e.g., <−20° C.) solvent such as ethanol is performed at atmospheric pressure. The dry sponges are then compressed, preferably to greater than about 0.4 g/cm$^3$ density and less than about 100 microns thickness. The preferred compression is not limited to but may include uni-axial compression between aligned flat platens, wherein the platens are heated between 18° C. and 150° C. and are pressure loading up to 10,000 bar.

The preferred compression creates a remarkably thin (e.g., range from about ≤50 microns to about ≤200 microns) strong (e.g., 5 MPa to 25 MPa UTS) readily foldable chitosan dressing that may be placed minimally invasively anywhere in the body in a confined folded form that can be reformed without compromised performance to the original unfolded dressing form for accurate and effective high surface area placement and attachment.

Figure 17:
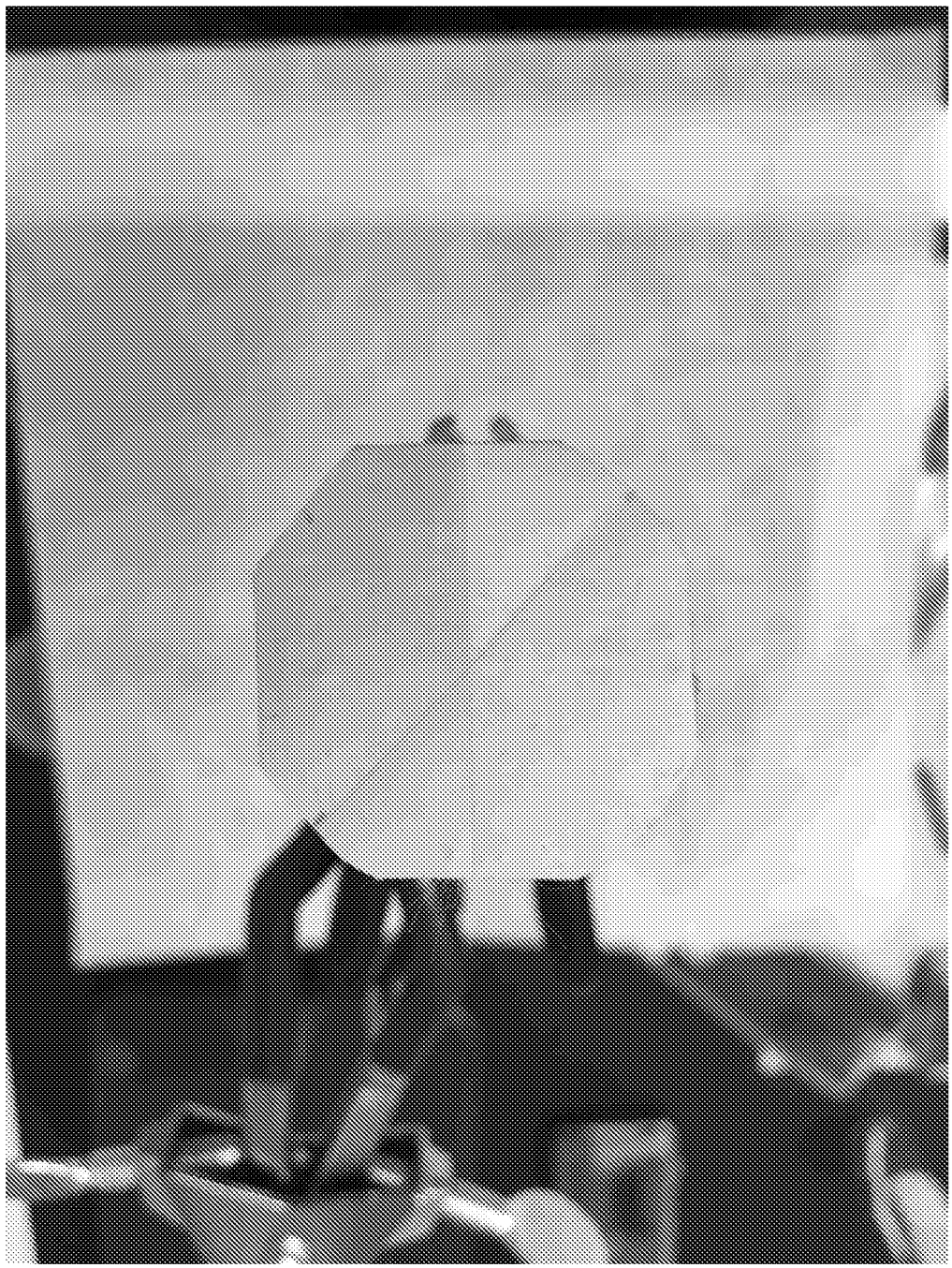
FIG. 17 depicts a catechol modified chitosan dressing that has been folded and unfolded, while remaining intact, with visible fold axis (crease).

Foldability is addressed in the examples below. In one embodiment, fold testing involved folding the horizontally planar final compressed circular dressing through 180° edge over edge, first in an anticlockwise direction, holding the edges together and compressing firmly in the middle of the dressing to create a single linear fold axis (or crease) in the dressing. The folded dressing is then opened and the edge to edge fold is reproduced in the new fold axis but with the folding in the opposite clockwise direction. Foldability success can be rated as no tears or cracks being visible along the fold axis and no significant loss in tensile properties of the dressing (determined by gentle pulling across the fold of the dressing). FIG. 17 shows a catechol modified chitosan dressing that has been folded and unfolded, remaining intact, with visible fold axis (crease).

Freeze phase separation of dilute aqueous polymeric solutions results in phase separation of micron and submicron thin polymeric chitosan lamella interspersed regularly between ice crystal sheets close to 200 microns in width. Removal of the ice by sublimation (freeze drying) or alternatively by solvent extraction leaves the dry sponge composed of close-to-aligned, thin (≤1 micron), polymeric chitosan lamella. Compression of the polymeric chitosan lamella at close to or greater than their glass transition temperature (Tg for dry chitosan is near 80° C.). allows for their compression into the thin (near 50 microns) dense polymeric structure formed of layers of hundreds of strong compliant polymeric chitosan leaves (lamella) which do not readily propagate cracks and which can be folded repeatably without failure. Such multi-leaf layering achieves remarkable strength. Prior to the present invention, no one has previously investigated high-density freeze-phase-separated chitosan dressings for manufacture and use as described herein and with the aim to address key problems solved by the present invention such as, for example, adhesion by removal of interfering fluids (by absorption, channeling, displacement, and/or re-direction), ability to form a fold axis and ability to resist mechanical failure on repeated folding and unfolding along the fold axis.

In one embodiment, porosity (void space>99%) is complete and uninterrupted in the non-compressed dressing with pore size range of 20-300 microns with substantially most of the pores near 100-200 microns. The un-interrupted pore structure is indicated in the compressed dressings by their ability to absorb biological fluid such as blood.

In some embodiments, crack free, clean edge holes near 500 microns in diameter may be formed in the dressing after compression by localized application of narrow gauge (near 500 microns in diameter), sharp pointed needle through the dressing and into a flat, hard elastomeric surface applied immediately against the dressing which may receive and release the point of the needle. Preferred receiving support flat surfaces include but are not limited to clean, dry thermoplastic elastomers with Shore 55D to 90D in hardness. Alternative methods of hole formation may include but not be limited to use of a small diameter (near 500 microns) hole punch or a laser cut hole.

In some embodiments, chitosan dressing provided herein has holes in the dressing. In some embodiments, the holes receive fiber or other reinforcing attachment elements. Such a reinforcing element may be formed by simple local application of a reinforcing fluid to locally bind with the edges of the holes. A reinforcing fluid used in the development of the present invention included cyanoacrylate glue which bound the compressed chitosan lamella of the dressing together and prevented local delamination and fibrillation of the chitosan at the hole stress point. Another embodiment of a hole reinforcing element is micro-molded interlocking parts of plastic or metal (dissolvable in the bladder or alternate area in the body of application) that are placed on one side of the hole and the opposite hole side to permanently fit together and be able to support load through the hole without causing dressing delamination, fibrillation or other stress related failure at the dressing hole when loaded. In some embodiments, the micro molded parts may include the part on the side of the attachment to a delivery device that enables convenient snap-on attachment and snap-off detachment of the dressing to the delivery device.

As used herein, the term fold axis is intended as part of the dressing sheet which demonstrates memory in the material of bending stress and or folding and is typically localized to narrow regions of high bending stress and shear. A crease in folded paper is an example of a fold axis.

In a preferred embodiment, the tissue adhesive component of the dressing is formed from a freeze phase separated and dried chitosan sheet with composition including a catechol chitosan. In a preferred embodiment the non-tissue adhesive component of the dressing is formed from a freeze phase separated chitosan dried sheet without any modified chitosan. In a preferred embodiment, both tissue adhesive and non-tissue adhesive dry sheets have density≤about 0.03 g/cm$^3$ before compression to final density≥about 0.4 g/cm$^3$.

In order to prepare one dressing from both sheets with the dressing having a tissue adhesive surface layer and a non-adhesive surface layer, the two sheets are bonded together by, for example, placing one sheet on top of the other and applying sufficient uniform pressure over the dressings to compress them to a higher density. In a preferred process, the original densities of each sheet type at ≤about 0.03 g/cm$^3$ is increased to a final dressing density≥about 0.30 g/cm$^3$. In a more preferred process, the original densities of each sheet type at ≤about 0.015 g/cm$^3$ is increased to a final dressing density≥about 0.4 g/cm$^3$. In a most preferred process, the original densities of each sheet type at ≤about 0.01 g/cm$^3$ is increased to a final dressing density≥about 0.5 g/cm$^3$. At the conclusion of the compression, the two compressed sheets are bonded together so that one cannot be readily peeled away from the other and the dressing can be manipulated by folding and furling without any occurrence of separation.

This physical adherence of materials by compression of two or more low density porous materials together to form a final two or more layer porous material of higher density solves a difficult problem of how to adhere such materials together without physical or chemical change to the individual materials and without addition of further bonding agents or adherents. It is contemplated that bonding may be attributed to microsurface impingement and penetration of the dressings through their pores with physical interlocking due to pore compression. This physical interlocking of low density, freeze phase separated, dry sheets is not restricted to two materials of the same thickness or to only two layers since the interlocking effect is neither sidedness nor thickness dependent. Therefore a multi-layered construct of individual freeze phase separated and dried sheets of the same or different materials of the same or different thickness may be formed by layering the low density sheets (preferably with density≤0.05 g/cm$^3$) and compressing the assembly together to a density≥0.3 g/cm3). Such a final physically adhered assembly would be expected to provide advantages of thin top and bottom surface layers including but not limited to adhering or anti-adhering materials with layers inside providing including but not limited to structural, physical and chemical elements.

In some embodiments, a chitosan dressing has an adhesive side and a non-adhesive side. In some embodiments, the adhesive side of the chitosan adheres to a tissue and absorbs and/or redirects the surface moisture. In some embodiments, the non-adhesive side detaches from a delivery device upon attachment of the chitosan dressing to the injury site wherein the chitosan dressing has become wet. This is in part because the adhesion strength of the chitosan dressing to the tissue surface controls the dressing location upon detachment of the dressing from the delivery device. Detach or "readily detach" as used herein in a two-sided chitosan dressing indicates that the chitosan dressing, with its adherent side applied to a tissue surface or an injury site and adhered due to absorbance of moisture, stays at the tissue surface or injury site while the non-adherent side releases from the delivery device, thereby allowing the delivery device to be retracted from the injury site without disrupting the position of the chitosan dressing on the tissue surface or injury site. In some embodiments, the chitosan dressing, when dry, attaches to the delivery device, thereby allowing delivery of the chitosan dressing along with the device onto an injury site.

In one embodiment, there is a need to attach the dressing locally to the delivery device. Generally, these local attachment areas are at the extremity of the dressing. For example, one design is to provide for local pinpoint attachment on the dressing extremity tabs at the circumference of the dressing and for no other attachment locations to avoid the risk of attaching the dressing to the delivery sheath, the delivery device, or itself (when furled/folded). The attachment locations may be designed to weaken when wet or alternatively be activated for release by some type of physical release mechanism.

In one mechanism, chitosan dressing provided in this disclosure is able to stop bleeding by absorbing, channeling, and/or redirecting the hydrophilic and hydrophobic fluids at an injury site. The absorption clears enough moisture from the injury site to allow subsequent hemostatic reactions between the chitosan dressing and the tissue at the injury site, which in turn stops bleeding and allows the chitosan dressing to stay attached; thus, sealing the injury site. The porous, dense, and multi-layer structure of chitosan dressing provided herein facilitates the absorption, channeling, and/or redirection of the moisture at the injury site, and the attachment or adherence of the chitosan dressing to the injury site.

The chitosan dressing disclosed herein is biocompatible. In some embodiments, the dissolved residue from a chitosan dressing applied to an injury site in vivo passes safely through the urethra and is excreted along with other bodily waste.

More than one, or multiple, chitosan dressings may be used or applied in serial fashion to a tissue treatment site or injury site. When more than one chitosan dressing is deployed, such dressings may separately adhere to adjacent tissue site or injury site areas, or may overlap with each other to varying extents. Due to the thinness of the chitosan dressing described herein, depending on the application, it is contemplated that multiple chitosan dressings may be used as needed to promote or achieve hemostasis of an injury site.

In one embodiment, the chitosan dressings overlap one another upon application. In such an instance, ideally there would be some adherence of the wetted adhesive side of the subsequent dressing to the wetted dressing backing of the earlier dressing. Accordingly, in one embodiment, the chitosan dressing does not have an anti-adherent backing but does have a backing with a weak wet adherence that provides for sufficient adherence for placement of a subsequent overlapping chitosan dressing.

A. Delivery Device

A delivery device, as used herein, is a device for delivering chitosan dressing. A delivery device delivers a chitosan dressing to injury sites at different locations in the body of an animal including human, pigs, dogs, etc.

In some embodiments, a delivery device is a minimally invasive device that can deliver a dressing, e.g., a chitosan dressing, to a physiological site in the body of an animal, in non-invasive or minimally invasive manner. In some embodiments, the delivery device is a balloon device. In some embodiments, the delivery device is a wire device or a device laser-cut from a small diameter cylinder of nitinol or stainless steel. In some embodiments, the non-invasive or minimally invasive feature of the delivery device is achieved through delivery of a dressing, e.g., a chitosan dressing, through a narrow catheter or a comparable working channel. In some embodiments, the balloon catheter or the comparable working channel has a diameter that is less than about 7 mm. In other embodiments, a channel of a TURP delivery device may range in diameter size from 5 mm to 7 mm.

Exemplary delivery devices include, but are not limited to, a balloon device, a balloon catheter, a wire device, a cylindrical device with laser-cut ends, a indwelling catheter, a urethral or suprapubic catheter, an external catheter, a short-term catheter, and an intermittent catheter.

A delivery device can also be a transluminal or transurethral delivery device. In some embodiments, the transurethral delivery device is non-invasive or minimally invasive due to a narrow catheter or tube/tubing or a similarly narrow-diameter portion of the device.

Delivery devices include other devices with narrow-diameter tubings or catheters or similar structures.

B. Attachment of the Dressing to the Delivery Device

TURP dressing attachment to the balloon is relatively simple.

In one embodiment, the circular dressing is folded once over itself edge to edge and then the folded dressing (now half) is folded once again edge to edge of itself (now a quarter). The dressing is unfolded and now there are two fold lines passing through the middle of the dressing. A tracing of the circumference of the catheter is drawn in the middle of the dressing (a small central circle). A scissors point or other sharp cutting instrument is used to cut along the intersecting fold lines in the middle of the dressing up to the drawn circumference of the catheter. Once the fold lines have been cut there are now four triangular windows or catheter connection tabs in the middle of the dressing. The catheter can be threaded thru the central opening in the dressing and the dressing tabs can be attached by double sided adhesive tape or other adhesive method of application to secure the tabs against the desired location of the catheter to set the bulk of the dressing over and against the catheter balloon. The dressing tabs are preferably placed on the side of the dressing facing away from the catheter balloon over which the dressing is to be folded. Preferably the adhesive used to attach the tabs to the catheter is water soluble to allow the dressing to slide off the catheter and be left in place (with optional catheter removal) after a pressure application by balloon catheter.

Applications and Methods of Treatment

The chitosan dressing provided in this disclosure may be used to stop bleeding in suitable diseases, conditions, disorders, or emergent traumas or injuries. In some embodiments, the dressing may be used to stop bleeding from any wet physiological surface, e.g. mucus. Exemplary applications include, but are not limited to, bladder bleeding, other intraluminal applications, including vascular applications, internal surgical bleeding, internal biopsy bleeding, internal bleeding following parenchymal organ resection, and oral, ocular, auditory or nasal bleeding. Additional applications that might require addition of water or fluid to encourage adhesion of the chitosan dressing to a tissue surface or injury site are also contemplated, for example, use of the chitosan dressing on external body surfaces.

Chitosan dressings of the present invention may be used for treatment of transurethral prostatectomy and or bladder neck bleeding that may include but not be limited to treatment of bleeding.

The various embodiments described above can be combined to provide further embodiments. All of the U.S.

patents, U.S. patent application publications, U.S. patent applications, foreign patents, foreign patent applications and non-patent publications referred to in this specification and/or listed in the Application Data Sheet, including U.S. Provisional Patent Application No. 62/612,003 filed Dec. 29, 2017, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

EXAMPLES

The following materials and preparations were considered in the chitosan endoluminal hemostatic dressing inventive process.

Chitosan A: Primex ChitoClear 65010, TM 4375, MW=250-300 kDa, Brookfield

Chitosan B: Primex ChitoClear 43000, TM 4167, MW=110-150 kDa, Brookfield viscosity in 1.0% w/w chitosan solution in 1.0% acetic acid at 25° C. and spindle LV1=9 cPs, DDA=95% (by colloidal titration).

Glacial acetic acid: Fisher Scientific, Catalogue No. A38-212.

Hydrochloric acid: 1.0 M aqueous solution Sigma Aldrich, Catalogue No. H9892.

L-Lactic acid: JT Baker, Catalogue No. 0196-01.

Glycolic acid: JT Baker, Catalogue No. M821-05.

Sodium hydroxide: 5.0 M NaOH aqueous solution Sigma Aldrich, Catalogue No. S8263-150 ml.

Potassium hydroxide: 0.1 M KOH in methanol (BDH).

Ethanol: 200° Proof Sigma Aldrich, Catalogue No. 459844-1 L.

Acetic anhydride: ACS reagent grade obtained from Sigman Aldrich, Catalogue No. 320102-1 L.

3,4-Dihydroxyhydrocinnamic acid (hydrocaffeic acid): 98% Sigma Aldrich, Catalogue No. 102601.

3,4-Dihydroxycinnamic acid (caffeic acid): 98% Sigma Aldrich Catalogue No. C0625 trans-3,4-Dihydroxycinnamic acid (trans-caffeic acid): Sigma Aldrich Catalogue No. 51868

3,4-Dihydroxyphenylacetic acid (DOPAC, Homoprotocatechuic acid): 98% Sigma Aldrich Catalogue No. 850217.

1-ethyl-3-(-3-dimethylamino-propyl)-carbodiimide: (alternatively N-(3-dimethylaminopropyl)-N'-ethylcarbodiimide hydrochloride with common acronym EDC) Sigma Aldrich, Cat. #E7750.

N-acetyl-L-cysteine Sigma Aldrich, Catalogue No. A7250

Sodium Chloride Sigma Aldrich, Catalogue No. 793566-500 g.

Glycerol: Sigma Aldrich, Catalogue No. G-8773.

Polyethylene glycol: Spectrum, Catalogue No. PO108.

Polyethylene oxide: Mw 400,000 da, Sigma Aldrich Catalogue No. 372773-500 G.

Poloxamer 407: Spectrum, Catalogue No. P1166.

Sucrose: Sigma Catalogue No. S3929.

D-Sorbitol: Sigma Catalogue S1876

Hydroxypropyl cellulose (HPC): Aldrich Catalogue No. 191892

Hydroxyethyl cellulose (HEC): Aldrich Catalogue No. 308633.

Synthetic urine formulation: Add calcium chloride dihydrate Sigma Catalogue No. C5080 (1.30 g); magnesium chloride hexahydrate Sigma Catalogue No. M2670 (1.30 g); sodium chloride Sigma Catalogue No. 793566 (9.20 g); sodium sulphate Aldrich Catalogue No. 238597 (4.60 g); sodium citrate dihydrate Sigma catalogue No. S4641 (1.30 g); sodium oxalate Sigma Catalogue No. 71800 (0.04 g); potassium dihydrogen orthophosphate Sigma Catalogue No. P5655 (5.60 g); potassium chloride Fisher Catalogue No. BP366 (3.20 g); ammonium chloride Sigma Catalogue No.09718 (2.00 g); urea Sigma catalogue No. U1250 (50.00 g); creatinine Acros Catalogue No. 228940500 (2.20 g) to a 2.0 liter volumetric flask and add 1.5 liters of deionized water to dissolve. After dissolution of ingredients in water and equilibration of solution temperature to room temperature, make up to 2.0 L mark with deionized water.

Porcine bladder with urethra, Animal Biotech Industries Inc., (Danboro, PA 18916)

Porcine small intestine casing, Butcher and Packer (29/32 mm) (Madison Heights, MI 48071)

Citrated bovine whole blood: Lampire Biological Laboratory Bovine CPD, Catalogue No. 7720010.

Cynaoacrylate A: Permabond 910 Tissue Adhesive, Catalogue No. 72590.

Cyanoacrylate B: Loctite 4902 instant adhesive Catalogue No. 1875841

Dialysis Tubing: 3,500 Da MWCO Snakeskin Dialysis Tubing (Fisher Scientific), Catalogue No. PI88244.

Parafilm: "M" Laboratory film, Pechiney plastic packaging (Chicago, IL 60631)

Adhesive: Double sided 3M Catalogue No. 21200-46144-6 (St Paul, MN 55144)

Scotch Fine Line Tape 218, 3M Catalogue No. 70-0060-4397-3 (St Paul, MN 55144)

Example 1

Preparation of Catechol Chitosan and Characterization

Figure 7:
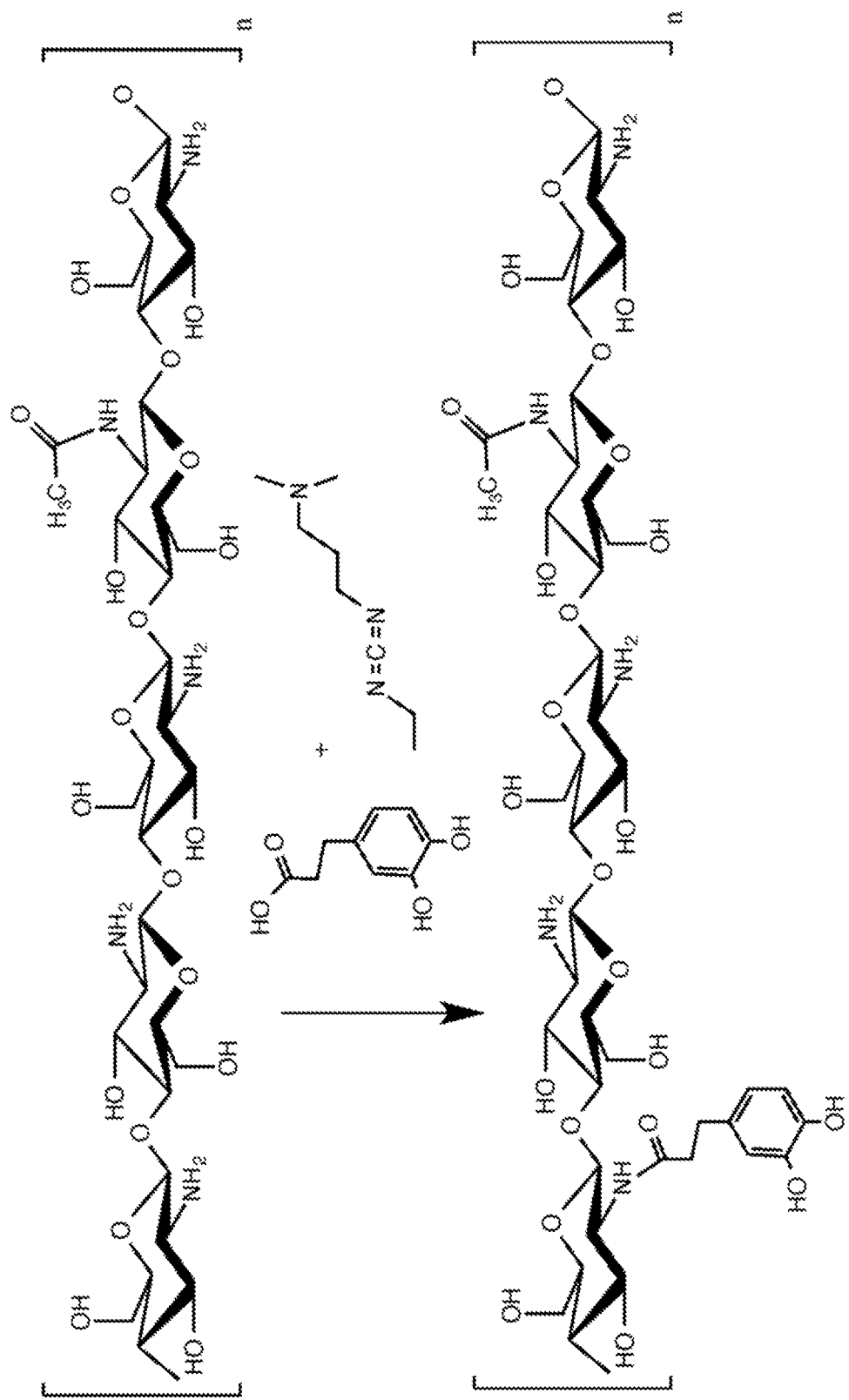
FIG. 7 depicts an N-acylation addition reaction in the presence of 1-ethyl-3-(-3-dimethylamino-propyl)-carbodiimide where 3,4-dihydroxyhydrocinnamic is covalently attached to a chitosan C-2 amine with a degree of substitution of 25% in aqueous solution at pH 5.5.
Figure 8:
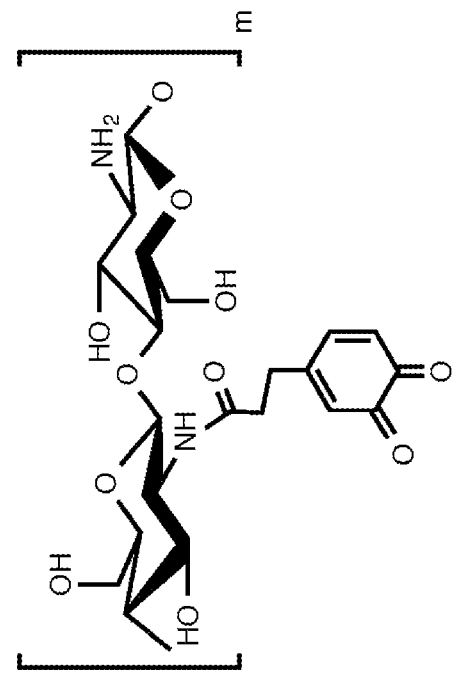
FIG. 8 depicts oxidation of catechol modified chitosan to ortho-quinone modified chitosan under elevated pH and in the presence of oxygen
Figure 8:
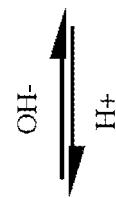
Figure 8:
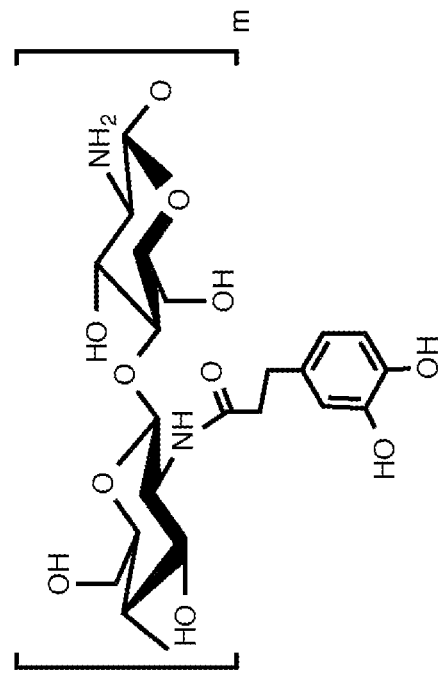

Catechol chitosan synthesis is an N-acylation reaction between a catechol molecule containing a terminal carboxylic acid and the C-2 amine of glucosamine mer of the chitosan (See FIG. 7). The reaction is performed at controlled pH in dilute aqueous solution at room temperature. FIGS. 14A and 14B 1 provide a number of examples of catechol modified formulations used in the preparation of the invention. Column 1 of FIG. 14B provides a list of dressing preparations. The formulations of the preparations are listed in column 2 of FIG. 14B. Catechol chitosan formulations have an acronym of "Cs-Cat". The Cs-Cat formulation number is provided immediately after the "Cs-Cat" and is written "Cs-Cat, XX" where XX is a numeric representing the catechol chitosan formulation number. Chitosan solutions were prepared and these are written as "Chitosan" or "Cs" typically with the acid (lactic or acetic) used to provide aqueous solution. HPMC is hydroxypropylmethyl cellulose. HPC is hydroxypropyl cellulose whereas HEC is hydroxyethyl cellulose. Chitosa lots are shown in column 3. The catechol degree of substitution of the chitosan (column 4 of FIG. 14B) was determined as follows:

Quartz UV test cells, 1 cm path length, ×2 (HACH Co., cat #48228-00) were used in acquiring UV/vis spectra. The UV/Vis spectrophotometer was a Varian Cary Bio 100.

Standard solutions of 3,4-dihydroxyhydrocinnamic acid were prepared in water and absorbance at 280 nm was plotted against concentration. The extinction coefficient ε in the Beer Lambert relationship shown below for absorbance in dilute solution $$A = \varepsilon \cdot c \cdot l$$

A is absorbance (dimensionless) and l is the path length (Absorbance<0.5) was determined as 2,540±50 liter/(mol·cm). This value was used to determine degree of substitution in the modified chitosan in dilute aqueous solution of known mass of modified chitosan, known volume of solution and measured peak absorbance at 280 nm.

The chitosan catechol solution is diluted so that its absorbance at 280 nm is less than 0.5 (usually about 1:50 or 1:100). The absorbance, the weight of the solution used in the dilution, and the percent solids (CS-catechol) were used to find the fractional degree of substitution ($f_{DS}$) of the HCA with respect to free amines on the chitosan backbone according to the equations:

$$f_{DS} = \frac{n_{HCA}}{f_{DDA} \cdot n_{total\ Chitosan\ mers}}$$

$$f_{DS} = \frac{A \cdot V \cdot \{(f_{DDa} \cdot 161) + (1 - f_{DDA} \cdot 203)\}}{\varepsilon \cdot l \cdot \left\{m_{cc} - \left(\frac{A \cdot V}{\varepsilon \cdot l} \cdot 165.17\right)\right\} \cdot f_{DDA}}$$

where A is UV/vis absorbance at 280 nm of the modified chitosan; V is the volume (liters) of the modified chitosan solution taken to dry to constant dry mass; $m_{CC}$ is the measured dry mass (g) of the catechol modified chitosan; $f_{DDA}$ is the fractional degree of deacetylation of the chitosan.

The percentage solute (primarily hydrophilic polymer) in the solutions is shown in column 5 of FIG. 14B. The depth of solution poured into the flat well mold for freeze phase separation is provided in column 6 of FIG. 14B. On freezing the depth of pour remains substantially unchanged so that after freeze drying the depth of pour provides a helpful indicator for the extent of compression change when referencing a the final set of the compressed dressing (provided in column 7 of FIG. 14B). The final density of the dry compressed dressing is provided in column 8 of FIG. 14B. Column 9 of FIG. 14B provides any additional information regarding the dressing preparation. It is interesting to note that the dressing 17 preparation was carried to a high degree of dryness while dressing preparations 71, 79, 80, 83, 84 and 85 were all performed with co-compression of a non-catechol chitosan dressing. These non-catechol chitosan dressings used as backings were all formed from 5 mm poured 43000 0.5% w/w chitosan acetic acid solution.

Examples of the catechol chitosan syntheses are given in the 6 approach variants provided below.

Approach 1
CS-Catechol, Batch 15:
Chitosan (1.51 g) was dissolved in deionized water (140 g) with 1.0 M HCl (5 mL). A 1:1 v/v solution (145 mL) of deionized water to ethanol was prepared. 3,4-dihydroxyhydrocinnamic acid (HCA; 10.5 mmol) and N-(3-dimethylaminopropyl)-N'-ethylcarbodiimide hydrochloride (EDC; 13.0 mmol) were dissolved in the water/alcohol solution. Next, the water/alcohol solution was slowly added to the chitosan solution prepared above and the reaction mixture was put on stirring. The pH of the reaction mixture was maintained at 5.5 using 5.0 M NaOH solution and left to react overnight. After reacting overnight, the solution was dialyzed against 5 L of deionized water acidified with 1 drop of 1.0 M HCl solution for three days and against deionized water for 4 hours. Dialysate was changed periodically (at least every 24-48 hours) throughout the duration of the dialysis.

Approach 2
CS-Catechol, Batch 22-1:
Chitosan (9.03 g) was dissolved in deionized water (126 g) with 1.0 M HCl (30 mL). The pH of the solution was then brought to 5.1 using 1.0 M NaOH solution. A 1:1 v/v solution (150 mL) of deionized water to ethanol was prepared and N-(3-dimethylaminopropyl)-N'-ethylcarbodiimide hydrochloride (EDC; 31.3 mmol) was dissolved in the water/alcohol solution. 3,4-dihydroxyhydrocinnamic (HCA; 15.7 mmol) was dissolved in of deionized water (15 mL). Next, the HCA solution was slowly added to the chitosan solution prepared above and the reaction mixture was put under overhead stirring. The EDC solution was then added slowly to the HCA/chitosan solution. The pH of the reaction mixture was maintained at 4.9 using 0.1 N KOH in methanol solution. After reacting overnight, the solution was dialyzed against 5 L of deionized water acidified with 1 drop of 1.0 M HCl solution for four days. Dialysate was changed periodically (at least every 24-48 hours) throughout the duration of the dialysis.

Some of the solution isolated from CS-catechol, batch 22 after dialysis was placed in an oven to concentrate the solution. The solution was baked at 80 C and the volume decreased by approximately one third.

Approach 3
CS-Catechol, Batch 32 (Prototype A, Acute In-Vivo I):
Chitosan (1.504 g) was dissolved in deionized water (143.5 g) with 1.0 M HCl solution (5.0 mL). The pH of the solution was then brought up to 5.5 with 1.0 M NaOH solution. A 1:1 v/v solution (150 mL) of deionized water to ethanol) was prepared and N-(3-dimethylaminopropyl)-N'-ethylcarbodiimide hydrochloride (EDC; 2.93 mmol) and 3,4-dihydroxyhydrocinnamic (HCA; 10.41 mmol) were dissolved in the water/alcohol solution. Next, the water/alcohol reactant solution was slowly added to the chitosan chloride solution. The pH was controlled between 4.9 and 5.5 during addition of the reactants to the chitosan solution using 1.0 M NaOH solution. After addition of the reactants, the reaction mixture was monitored for 2-4 hours and the pH was controlled between 5.4 and 5.7 using drops of 1.0 M HCl and 1.0 M NaOH as needed. Next, pH was controlled to 5.5 and left to react overnight. After reacting overnight (approximately 18-24 hours), the pH of the chitosan catechol solution was controlled back to 5.5. Next, the chitosan catechol solution was dialyzed against 5 L of deionized water at approximately pH 5.8 for 5 days, and against deionized water at approximately pH 6.1 for 4-24 hours. Dialysate was changed periodically (at least every 24-48 hours) throughout dialysis procedure.

Approach 4
CS-Catechol, Batch 33
Chitosan (0.507 g) was dissolved in deionized water (47.5 g) with 1.0 M HCl solution (2.0 mL). The pH of the solution was brought up to 5.5 using 5.0 M NaOH solution. A 1:1 v/v solution (50 mL) of deionized water to ethanol was prepared and N-(3-dimethylaminopropyl)-N'-ethylcarbodiimide hydrochloride (EDC; 2.94 mmol) and 3,4-dihydroxyhydrocinnamic (HCA; 1.49 mmol) were dissolved in the water/alcohol solution (—reactant solution—). Next, the reactant solution was slowly added to the chitosan chloride solution. The pH was controlled between 5.4 and 5.6 for 2.5 hours. Then, the pH was controlled down to 5.4 and left to react overnight (approximately 18-24 hours). The resulting chitosan catechol solution was pH controlled to approximately 5.5 and subsequently dialyzed at approximately pH 5.8 for 3 days and deionized water for 3 days. The dialysate was changed periodically throughout the dialysis procedure. After dialysis, the solution was allowed to evaporate excess water gained during dialysis by hanging the solution in the dialysis tubing in a fume hood overnight. The solution was left until it returned to its pre-dialysis weight.

Approach 5
CS-Catechol, Batch 35

Chitosan (1.681 g+10.6% w/w moisture) was dissolved in deionized water (143.5 g) with 1.0 M HCl solution (11 mL). The pH of the chitosan chloride solution was then brought up to approximately 5.5 with 1.0 M NaOH solution. A 1:1 v/v solution (150 mL) of deionized water and ethanol was prepared and N-(3-dimethylaminopropyl)-N'-ethylcarbodiimide hydrochloride (EDC; 8.76 mmol), 3,4-dihydroxyhydrocinnamic (HCA; 2.39 mmol), and N-acetyl-L-cysteine (NAC; 2.36 mmol) were dissolved in the water/alcohol solution (—reactant solution—). Next, the reactant solution was added to the chitosan chloride solution. The pH of the reaction mixture was controlled between 5.2 and 5.3 during the addition of the reactant solution. After 2 hours, the pH of the reaction mixture was brought up to approximately 5.4. The solution was then left to react overnight (approximately 18-24 hours). After reacting overnight, the pH of the solution was controlled up to approximately 5.5. The solution was dialyzed against 5 L of deionized water for 6 days. The dialysate was changed periodically (at least every 24-48 hours) throughout the dialysis procedure.

Approach 6
CS-Catechol, Batch 38

Chitosan (1.678 g+10.6% w/w moisture) was dissolved in deionized water (143.3 g) with 1.0 M HCl solution (8 g). The pH of the chitosan chloride solution was then brought up to approximately 5.5 with 1.0 M NaOH solution. A 1:1 v/v solution (150 mL) of deionized water and ethanol was prepared and N-(3-dimethylaminopropyl)-N'-ethylcarbodiimide hydrochloride (EDC; 2.95 mmol), 3,4-dihydroxyhydrocinnamic (HCA; 1.475 mmol) were dissolved in the water/alcohol solution (—reactant solution—). Next, the reactant solution was added to the chitosan chloride solution. The pH of the reaction mixture was controlled at close to pH 5.5 during the addition of the reactant solution. After 2 hours, the pH of the reaction mixture was adjusted up to 5.51. The solution was then left to react in a covered beaker a room temperature for 20 hours. After 20 hours, the pH of the solution was 5.54. The solution was divided into 3 lots of close to 100 g solutions in dialysis tubing and dialyzed against 5 L of deionized water for 5 days with pH at 5.8-5.9 on the first 3 days and pH 6.2 on the fourth day. The dialysate was changed regularly (every 24 hours) throughout the dialysis procedure.

Example 2

Freeze Phase Separated Hydrophilic Polymer Dressings

Hydrophilic polymer aqueous solutions were prepared inside 500 ml, 1000 ml or 2000 ml Nalgene LDPE bottles or polypropylene beakers by addition of components including but not limited to pre-prepared solution, hydrophilic polymer, water, acid, and additional components. FIG. 14B lists 85 of the formulation types that were investigated.

The main problems experienced when formulating for the transuretheral prostatectomy application with dressings in direct contact with urine were: 1) rapid (generally <30 mins) urine promoted dissolution of chitosan; 2) interference from blood in achieving rapid adherence with the pure catechol modified chitosans; 3) susceptibility to dressing cracking and tearing when making changes to formulations to address problems with dissolution and adherence. The final hydrophilic polymer solution % w/w was between 0.1% to 4% by weight polymer. Capped bottles and their contents were mixed continuously at room temperature over 12-24 hours to achieve full solution homogeneity using IKA KS260 orbital shaker or a Wheaton bench top bottle roller. Beaker solutions were mixed on a magnetic stirrer plate with magnetic stirrer bead at room temperature for 12 to 24 hours to achieve solution homogeneity. Parafilm was used to close the beaker from the external environment during mixing. The solutions prepared for freeze phase separation were substantially homogeneous and clear when suspension conditions were not present. The catechol chitosan solutions demonstrated some haze and milky appearance indicating presence of some dispersed fine catechol chitosan globular particles.

Chitosan solutions were prepared as freeze phase separated dressings with final solution % weight of hydrophilic polymer in the range 0.25% to 4% w/w aqueous solution. Freeze phase separation was performed in Teflon coated aluminum mold wells with horizontal flat bases. The solutions were poured into the wells to a height from the mold base of preferably not more than about 10 mm, more preferably 2.5 mm and most preferably 5.0 mm. The solutions initially at a temperature in the molds before freezing between 15° C. and 30° C. were then frozen by application of cooling through the base of the molds. Although other cooling temperatures may be applied to achieve suitable freeze phase separated structure, preferably the applied cooling temperature of the shelf was −40° C., more preferably the cooling temperature was −55° C. and most preferably the cooling temperature was −45° C. After the solution achieved freezing phase separation and the temperature of the frozen solution equilibrated at the freezing temperature, the system was allowed to further freeze phase separate and equilibrate for at least an additional hour before drying. In a modified freezing and mold filling method to accommodate layers of different freeze phase separated solutions, a first layer was added to the mold to a preferred depth and frozen, a second layer was then added and frozen, a multilayered freeze phase separated dressing could be prepared in this manner. Care was needed to ensure there was no frost between an (n−1)th frozen and nth poured solution and differences in layer frozen structure could result in cracking. Layering of separate frozen layers adhering together and not cracking is a significant problem. The discovery of the successful method of layering and adhering of single layer previously dried hydrophilic polymer matrices to a single co-adhered compressed multilayered composite sheet during this investigation was an unexpected and significant finding.

A 24 square foot shelf Virtis Benchmark 2000 pilot scale freeze dryer was used for sublimation freeze drying of the freeze phase separated frozen solution plaques. In the primary freeze drying (removal of ice not hydrogen bonded to the hydrophilic polymers), the equilibrated frozen plaques in their molds were subjected to reduction in pressure≤300 mTorr within the freeze dryer, the freeze dryer condenser was set to ≤−65° C. and the freeze dryer shelves were heated to promote sublimation of the ice from the freeze separated plaques without increasing plaque temperature above −15° C. After removal of substantially all the non-bonded ice, the shelf temperature was raised to near 25° C. for removal of the hydrogen bonded ice and reduction of moisture content in the dried dressing matrix to not more than 4% residual water in the dried dressing matrix. Final dried matrices conformed to the original shape of the filled mold with close to 5% shrinkage in length and width and density between 0.005 g/cm3 and 0.04 g/cm3. They contained void space of more than 95% and they were interconnected porous structure with fine polymer lamella (submicron to 5 micron thickness) and pore spacing between adjacent lamella of 100 microns to 300 microns.

After freeze phase separation and drying, the dried matrices were compressed from their original thicknesses (10 mm to 2.5 mm) to a final thickness preferably near 50 microns. If two uncompressed dressings were compressed one on top of the other then they would be permanently bonded together at the conclusion of the compression process. Calibrated uniform thickness thin shims may be used in the compression to achieve a desired thickness of compressed dressing substantially the same thickness as the shim. There are a number of ways to achieve this compression with a desired compression set near 50 microns. The preferred compression method used in the investigation was compression of the whole dried uncompressed dressing (dimensions typically close to 100 mm long×100 mm wide×2.5 mm high or 50 mm diameter×2.5 mm high) with uniaxial compression rate at ≤0.5 mm/min to ≤100 microns thickness between aligned platens. The platens (Diamond sprayed or Teflon coated Mic 6 Aluminum 300 mm×300 mm×90 mm) were machined to flat planar faces (≤5 microns in 300 mm) with none or some controlled texture machined into their surface. The temperature of platens during compression was maintained preferably near 80° C over 3-5 minutes of uniaxial compression. Compression was achieved by screw loading at the four corners of the platens at up to four tonnes loading at each corner. Compression was held for at least 2 minutes before release of load. The novel compressed hydrophilic polymer matrices were measured for compression thickness and weight. Final densities were between 0.25 and 0.9 g/cm$^3$. After compression, the dressings were further processed. This additional processing included die cutting into 2.5 cm diameter test pieces and in some cases thermal annealing heat treatment (heated in a convection oven at 60° C.-150° C. for 5-30 minutes). At the conclusion of processing the dressings were placed in foil pouches with zip lock or thermal sealing. Packaged dressings intended for animal and biocompatibility testing were gamma-irradiated at 25 kGy.

Example 3

In Vitro and Ex-Vivo Testing of Chitosan Endoluminal Hemostatic Dressing Prototypes In Vitro Beaker Test The dissolution behavior of the CEHD was investigated under conditions similar to those that would be experienced during TURP in vivo use. Dissolution was monitored for periods up to 7 days to establish that the CEHD dissolution met targeted resistance to early dissolution (in the first 24 hours) with subsequent later dissolution so that no residual CEHD would be present after 168 hours (7 days).

Sectioned pieces (25 mm×25 mm×3 mm) of porcine bladder tissue with mucosal surface facing outwards were fixed with cyanoacrylate cement to the bottom of a 200-milliliter polystyrene beaker. One drop of solution of 1:250 v/v blood in standard saline was onto the top surface of the ex-vivo sectioned bladder tissue. A CEHD dressing piece (1.3 cm×1.9 cm) was applied with 9.7 kPa (73 mmHg) pressure to the wetted tissue surface by application of a 500-gram standard weight (Troemner, Thorofare NJ 08086) onto a 2.54 cm diameter probe for 5 minutes. Sufficient synthetic urine (50 ml) at room temperature was added to the beaker to submerse the CEHD pieces. The beaker was covered with Parafilm, incubated (Fisher Scientific Model 146E, CAT. 97-990E) at 37° C., and placed on a shaker (IKA AS260.1, KS 260) at 120 rpm. The synthetic urine solution was changed every 24 hours and dissolution behavior was documented by amount of dressing visually present at regular intervals until complete dissolution, or up until 168 hours. In some tests, CEHD test piece adhesion to tissue was evaluated by a horizontal scraping movement of tweezers to measure resistance to sheer force. The CEHD tissue adhesion testing was performed during the in-vitro dissolution testing on a pass or fail basis, and noted as low, moderate, or high.

The results of in vitro dissolution and adhesion to porcine bladder mucosa are shown in FIG. 15. The in vitro dissolution and adhesion to porcine bladder mucosa results were used together with results of folding and device deployment testing to select three preferred dressing types for biocompatibility and in vivo testing. These dressing types included catechol modified chitosan preparations and preparations of both catechol and thiol chitosan modification. The preferred pre-in-vivo dressing types were labelled types A, B and C. Dressing Lots 71 and 81 representing type A dressings; Lots 78 and 83 representing B type dressings and Lots 75, 80 and 84 representing type C dressings.

In-Vitro Simulated Venous Wound Sealing (SVWS) Testing

A laboratory simulated venous wound sealing (SVWS) device was built to test the sealing ability of the CEHD adhered by one drop of dilute blood, 1:250 v/v blood in standard saline, with 9.7 kPa load for 5 minutes over a 1.5 mm diameter "injury" aperture in the center of a standard PVC plate whose surface had previously been shown to mimic dermis with respect to mucoadhesive chitosan binding to dermis. Silastic Laboratory Tubing, Size—0.250 in I.D.×0.375 in O.D., Dow Corning Corporation (Midland, MI 48686) connected an open reservoir of citrated bovine whole blood to the aperture with a stopper valve immediately before the aperture. The vertical height of the blood level in the reservoir relative above the aperture was adjustable from 0.0 to 50 cm. After a CEHD test dressing was attached centrally over the aperture in the standard PVC surface the stopper valve was opened and dressings were observed for 15 minutes and assessed (pass/fail) on their ability to maintain sealing (absence of blood leakage through or under the attached dressing). The pressure head was noted in each test. This test provided rapid simulated bleeding control testing of prototype CEHD's under venous bleeding pressure.

Simulated bleeding rate (g/min) was determined by weight difference between a pre-weighed absorbent sheet and the same absorbent sheet placed over the "injury" collecting flowing blood for 15 seconds and multiplying by 4.

A 20 cm to 42 cm head height difference at 23° C. is equivalent to 14.7 mmHg to 30.9 mmHg pressure (typical of venous pressure in prostatic bleeding). Bleed rates for the 20 cm and 42 cm height differences were determined as 4.7 and 8.0 g/min respectively.

Results of in-vitro simulated venous wound sealing (SVWS) testing are provided in Table 1 of 25 kGy gamma irradiated dressings Lots B and C (with shelf life in foil packaging at 25° C. temperature storage for 0 and 6 months).

TABLE 1 in-vitro simulated venous wound sealing (SVWS) test results.

| Shelf-life (months) | Dressing type | Height (cm) | Test 1 | Test 2 | Test 3 | Test 4 | Test 5 |
|---|---|---|---|---|---|---|---|
| 0 | C | 21 | Pass | Pass | Pass | Pass | Pass |
| 0 | B | 21 | Pass | Pass | Pass | Pass | Pass |
| 6 | C | 21 | Pass | Pass | Pass | | |
| 6 | B | 21 | Pass | Pass | Pass | | |
| 6 | C | 42 | Pass | Pass | Pass | Pass | Pass |
| 6 | B | 42 | Fail | Fail | Fail | Fail | Fail |

Figure 10:
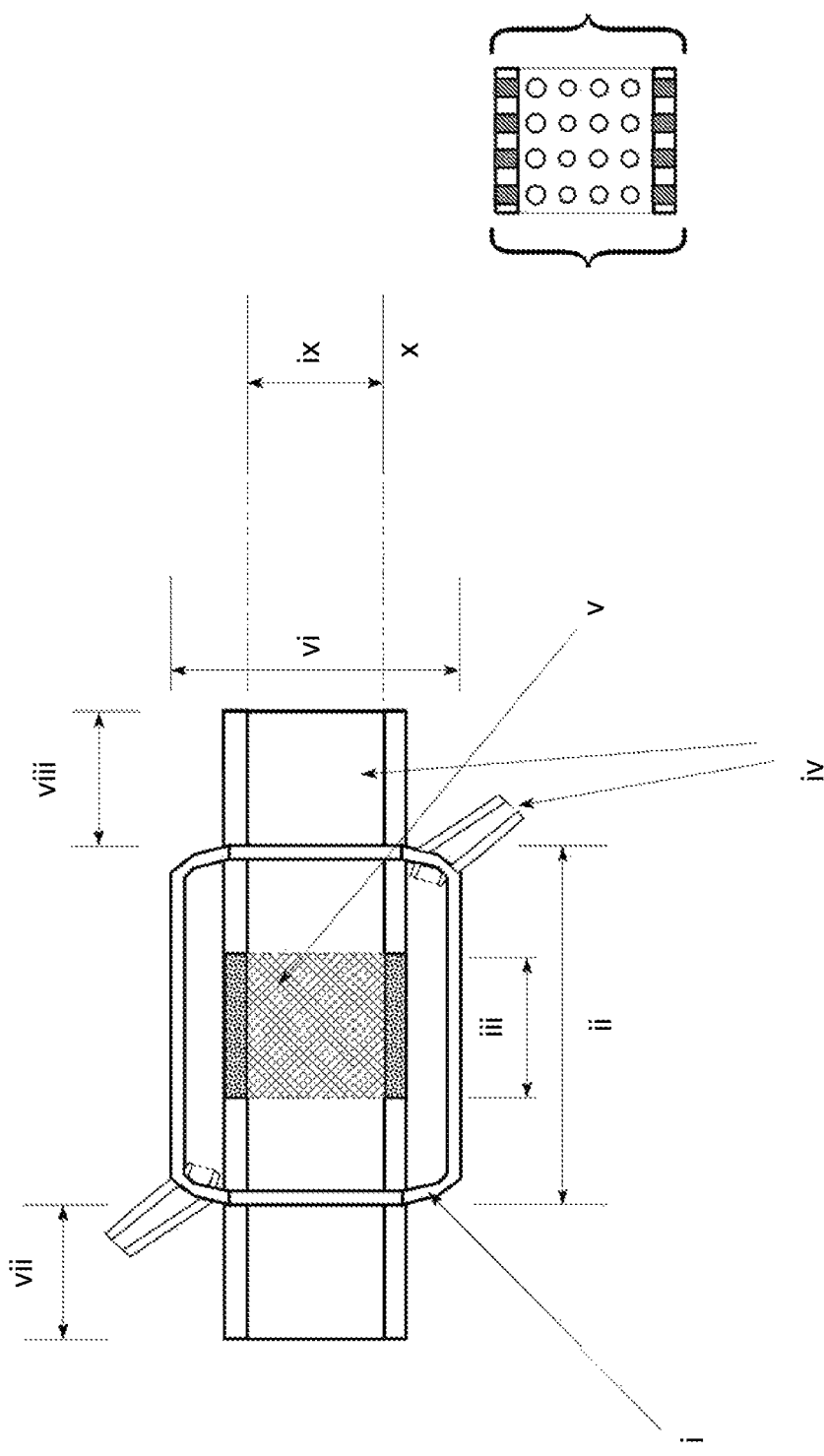
FIG. 10 depicts a glass flow cell 4 cm long and 1.5 cm internal diameter capable of supporting a 6 cm long 1.5 cm diameter stretched tube of porcine small intestine submucosa by wrapping over the ends of the cell and applying pressure ties; i is glass jacket; ii is 4 cm; iii is 1.6 cm; iv is glass fixture for tubing connection; v is perforated glass cylinder region between ring clamps; vi is ca. 3.2 cm; vii is 1.5 cm; viii is 1.5 cm; ix is (Schott) 1.5 cm ID; x is 2.5 mm tube wall.
Figure 11:
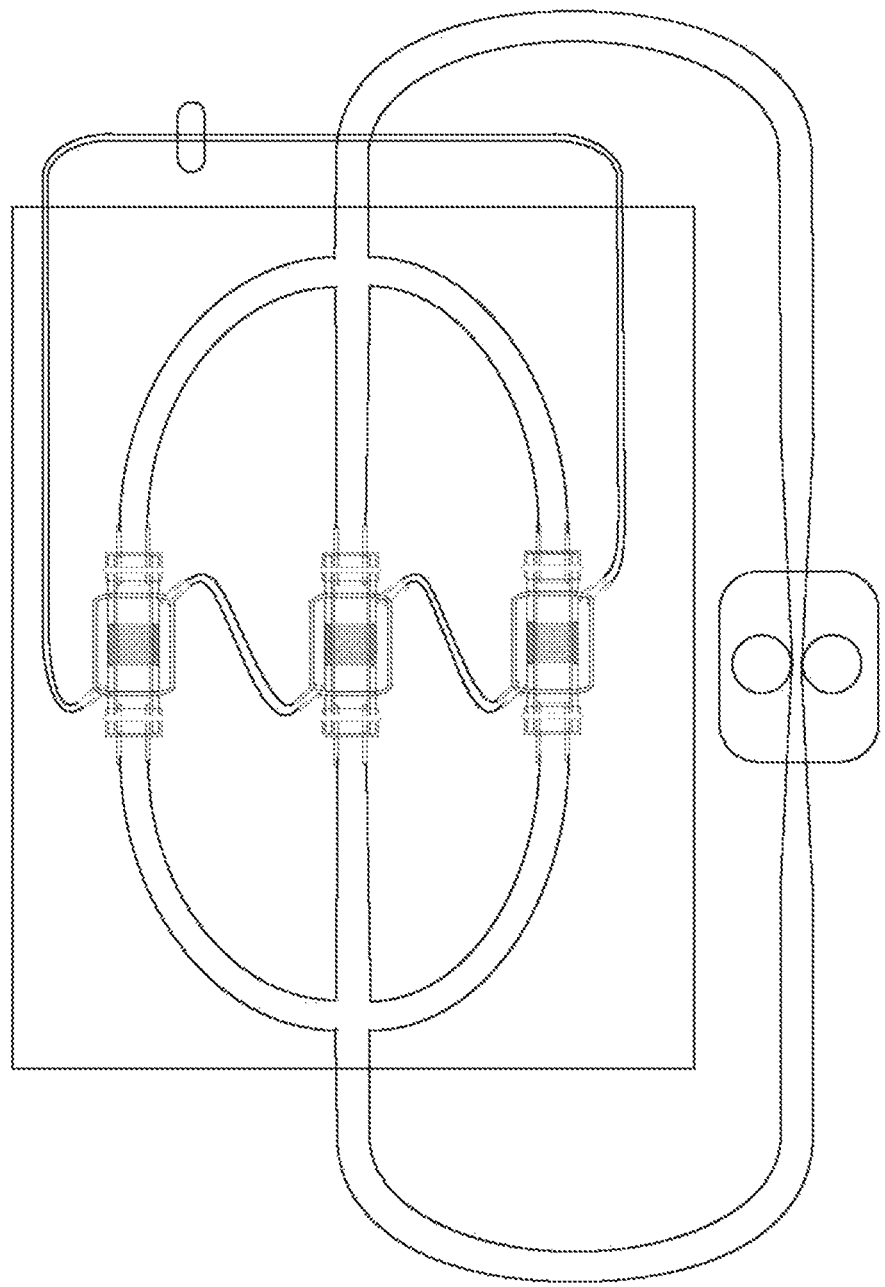
FIG. 11 depicts a typical flow cell design (with 3 cells attached in parallel) for testing adherence and dissolution resistance under urine flow at 37° C. of novel dressings adhered to cell supported ex vivo tissue surfaces.
Figure 12:
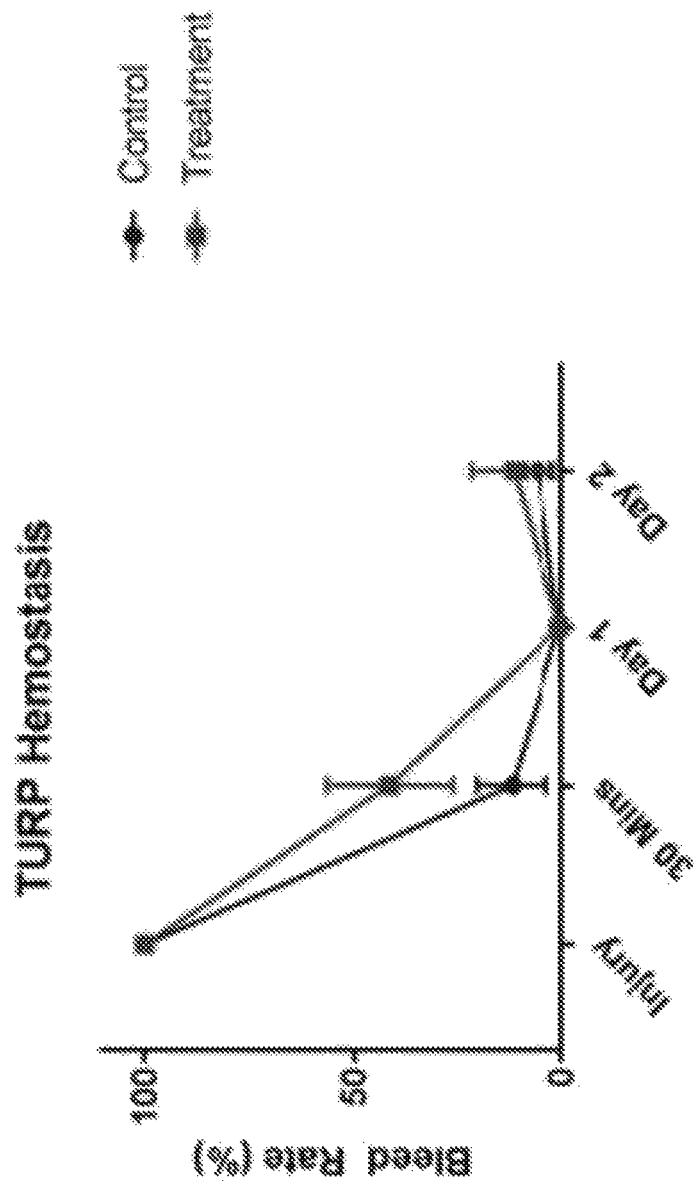
FIG. 12 shows the mean bleeding rates in the bladder injury model of a preferred embodiment device of the invention (balloon and dressing combined with delivery balloon deflated after application) compared to standard of care control (balloon device without dressing but remaining inflated against injury).
Figure 13:
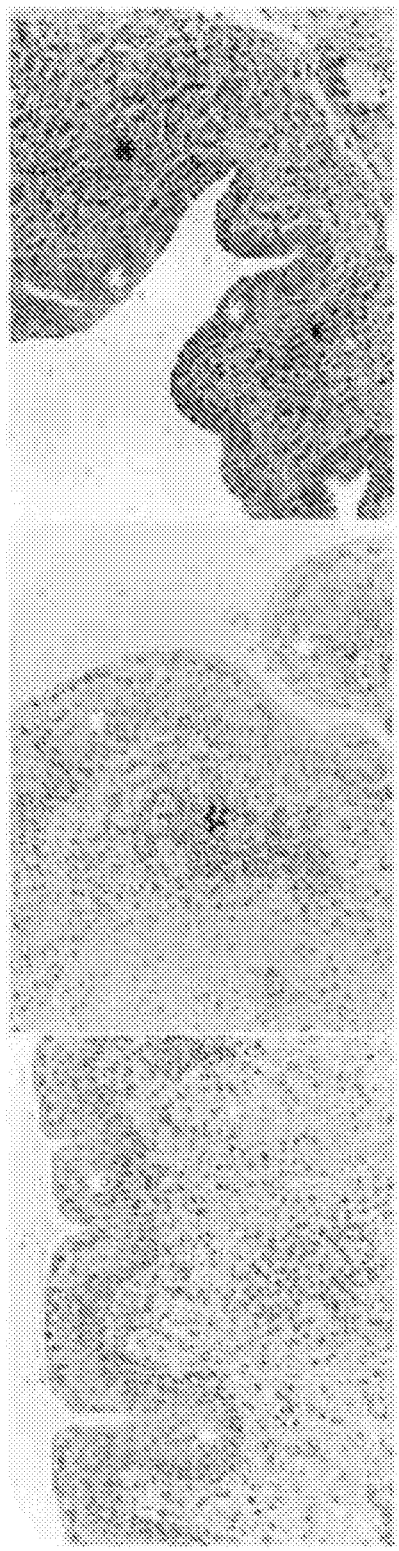
FIG. 13 shows histological wound healing at 7 days of control and preferred embodiment device of the invention.

Ex-Vivo Flow Testing of 10 mm×10 mm Dressing Adhered Over 3 mm Diameter Perforation in SIS Test dressings that performed well in vitro (dressing types B and C, N=10 each)—see FIGS. 14A, 14B and 15) were adhered under balloon pressure near 7 psi for about 3 minutes to porcine small intestine submucosa (SIS) centrally over a 3 mm diameter hole in the SIS supported in an Adams and Chittenden custom manufactured glass test cell (see FIG. 10). The test cell containing the dressing adhered to the SIS sealing the defect was connected to the flow system depicted in FIG. 11. A Fisher Scientific FH100M multichannel peristaltic pump with 13-310-911 flow cassettes was used to provide a controlled rate of flow near 20 ml/min. Synthetic urine near 34° C. to 37° C. and fully filling the volume of the cell was flowed through the cell at close to 20 ml per minute for 6 to 20 hours. The purpose of the testing was to demonstrate ability of the dressings to remain adhered to mucosa under flowing urine without tearing or loss of particles or larger pieces from the dressing.

In the case of dressing Type C (dressing Lots 75 and 80), one test was performed for 20 hours. At the conclusion of the testing, an external pressure of 1:250 v/v blood in standard saline near 20 mmHg was applied through the jacketed circuit of the glass test cell to test the adherence of the test dressing to the tissue. The application of pressure was applied 4 times and the dressing successfully remained adhered over the 3 mm diameter hole to the internal SIS surface resisting the external application of fluid pressure on all 4 pressure applications. This 20 hour tested dressing was also examined for loss of mass (by gravimetric comparison of dry weight before and after testing). The gravimetric testing of type C dressing after 20 hours showed that material loss of catechol modified chitosan (most likely by dissolution) was ≤15% by dry weight of the original dressing. All other tests for the type C dressings were performed for 6 hours without application of the external pressure stress. In the case of the type C dressings, there was no significant visible dissolution of dressing or any loss of material from the dressings. All dressings remained adhered to the SIS at the end of testing. The adhesion (to SIS mucosa) and cohesion of the dressings were rated as moderate.

In the case of dressing Lot Type B (dressing Lots 78 and 83) one test was performed for 24 hours. This 24 hour tested dressing was examined for loss of mass (by gravimetric comparison of dry weight before and after testing). The gravimetric testing of type B dressing after 24 hours showed that material loss of catechol modified chitosan (most likely by dissolution) was significant at 39.4% by dry weight of the original dressing. All other tests for the type B dressings were performed for 6 hours. In the case of the type B dressings, there were visible indications of significant dissolution of dressing (gelling) and loss of material (visible pieces being released from dressing) from the dressings. The adhesion (to SIS mucosa) and cohesion of the dressings were rated as moderate to low.

Example 4

Foldability and Deployment Testing of Dressing

All dressing Lots (N≥3) were tested for foldability because this is an important characteristic for ability to attach, furl and deploy the dressing of the invention against prostatic and bladder neck injury sites. Fold testing involved folding the horizontally planar final compressed circular dressing through 180° edge over edge, first in an anticlockwise direction, holding the edges together and compressing firmly in the middle of the dressing to create a single linear fold axis (or crease) in the dressing. The folded dressing is then opened and the edge to edge fold is reproduced in the new new fold axis but with the folding in the opposite clockwise direction. Foldability success is rated as no tears or cracks being visible along the fold axis and no significant loss in tensile properties of the dressing (determined by gentle pulling across the fold of the dressing). Results of the foldability testing are provided in column 4 of FIG. 15.

Deployment testing (N=5) was performed with preferred chitosan backed dressing types A, B and C using a 250-milliliter volumetric flask filled with normal saline as a model of a urine filled bladder neck. A fully assembled device with CEHD dressing, sheath covering and balloon catheter (distal and proximal balloons) was submerged in the normal saline below the neck of the volumetric flask. The CEHD application was initiated by inflating the distal balloon to break the protective waterproof sheath at its distal end, followed by manual complete and intact removal of the torn sheath by pulling on its dry free end outside the flask, swift positioning of the distal balloon at the bladder neck followed quickly by smooth and rapid inflation of the proximal balloon to open and adhere the dressing against the flask neck. All dressing types (A, B and C) were delivered successfully with good adhesion to the glass vessel neck.

Example 5

Biocompatibility of Dressing Types

ISO 10993-1 biocompatibility testing of finished, packaged, sterile (terminal gamma irradiation at 25 kGy) devices was conducted according to testing requirements for external communicating devices with indirect blood path contact for limited contact. The tested included cytotoxicity, dermal irritation and acute systemic toxicity (in triplicate for each test).

Dressing types A and C passed all the biocompatibility testing while dressing type B failed the acute systemic toxicity testing. It is suspected that gamma irradiation produced a cytotoxic thiol residue in the type B dressing.

Example 6

Acute In Vivo Bladder Neck and Swine Splenic Capsular Stripping Models of Hemostasis Acute in vivo testing was performed in six domestic female Yorkshire swine, body weight 40-50 Kg (Oak Hill Genetics, CA) and the delivery device was assembled with the three CEHD prototypes (Dressing A: n=6; Dressing B: n=9; Dressing C: n=10). The experiment was designed as a blinded randomized study of efficacy of individual prototypes vs controls in acute swine bladder neck and splenic parenchyma bleeding injury models.

TABLE 2

Study results acute in vivo

| Conditions | Dressing A | Dressing B | Dressing C* | Control |
|---|---|---|---|---|
| Adherence score in vivo (0-4)‡ | 1.75 ± 0.29 | 1.58 ± 0.91 | 1.7 ± 0.97 | |
| Initial bleeding rate at 5 min (ml/min) in bladder neck injury | 0.035 ± .007 | 0.032 ± .027 | 0.039 ± .031 | |
| Bleeding rate after applied CEHD at 2 hrs in bladder neck injury (ml/min) | 0.0045 ± .0029 | 0.0042 ± .0034 | 0.0034 ± .0011 | |
| Hemostasis at 30 sec in splenic injury mode (ratio) | 1/12 | 3/12 | 5/12 | 0/12† |
| Hemostasis at 3 min in splenic injury mode (ratio) | 6/12 | 7/12 | 4/12 | 6/12† |

*Dressing C was selected to advance to a seven day survival study.
‡0, 1, 2, 3 and 4 = no (material does not adhere), low (adheres but is easily dislodged), moderate (can be removed by probing at edge), moderate to strong (resists removal by probing edge), and strong (probe cannot dislodge edge) adherence respectively.
†Surgical gauze was used as negative control for splenic injury model.

Example 7

Seven-Day Survival Study of Control Urethral Hemorrhaging Using Final CEHD Device The final CEHD prototype delivered by double balloon catheter device was tested in vivo over 7 days against a conventional single balloon Foley catheter with no CEHD in a prospective randomized study in two ten animal groups with bleed rate determined by hematuria in the urine prior to injury, 30 minutes after injury, at 1 day and at 2 days. After the bladder neck injury was made, the control or test materials were placed at the injury site. In the case of the test article CEHD, initial balloon pressure and traction were maintained for 3 minutes after which the traction and balloon pressure were removed. In the case of the control Foley catheter the balloon pressure and traction were applied against the wound as same as for CEHD deployment.

Figure 9:
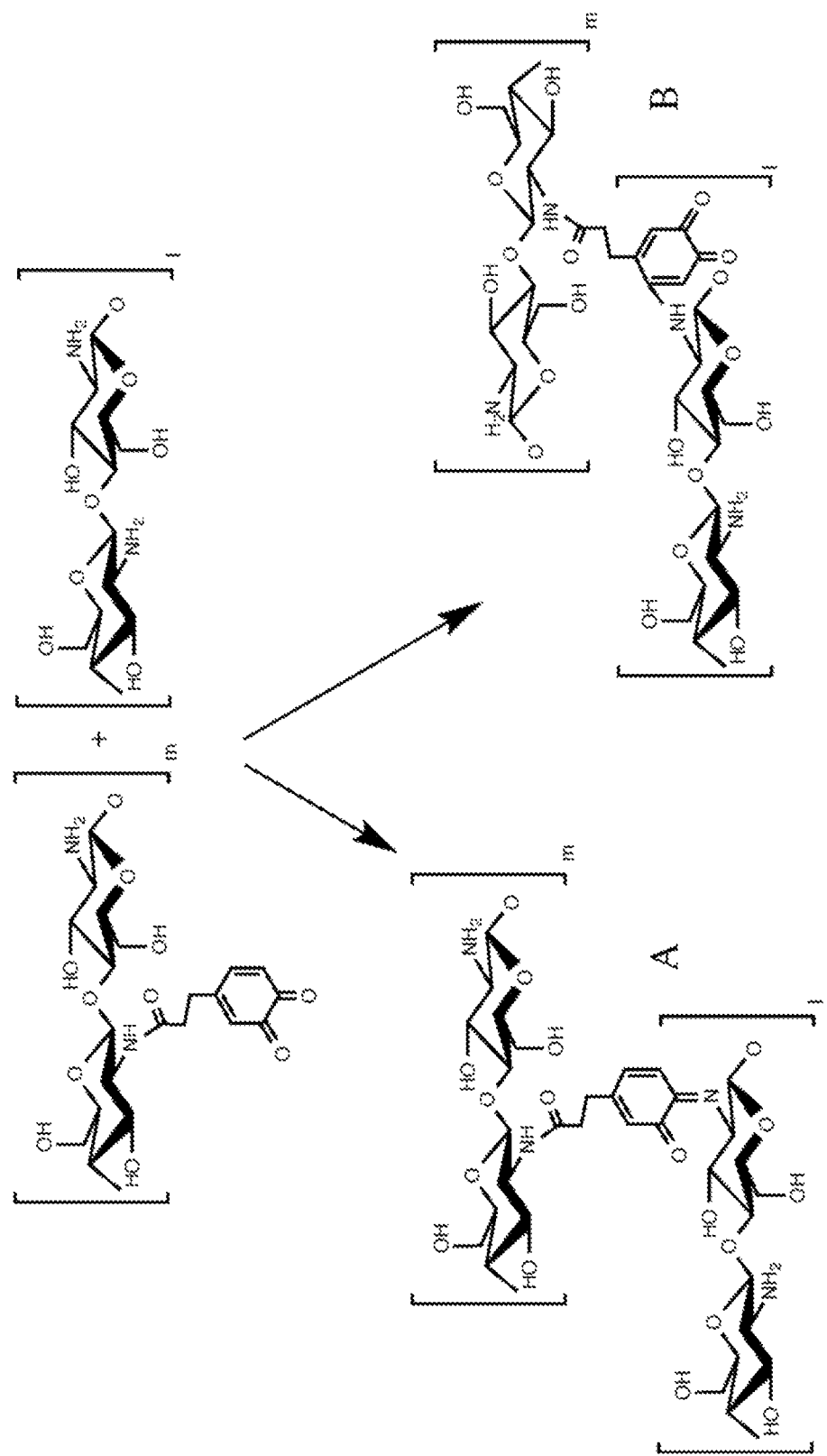
FIG. 9 depicts Schiff base (A) and Michael addition (B) reactions causing crosslinking between catechol modified chitosan and chitosan.

Of twenty swine, four (2 in each arm) were euthanized early and excluded from study due to surgery related adverse events including which 3 had bladder neck/urethral perforation during creating the injury model and 1 had tracheal perforation during anesthesia intubation. None of the control or test swine demonstrated material related adverse responses. The following results were obtained from the study: 1) Bleed rates decreased significantly in both cases of balloon compression with or without CEHD. There was no statistically significant difference between the CEHD group and control group (FIG. 9) with respect to bleed rates. 2) Histology study showed the bladder neck wounds healed well at 7 days in both study groups (FIG. 10). No CEHD residuals were found at day 7. 3) Animals in both groups demonstrated good health over 7 days of monitoring, with no signs of adverse events that related to CEHD device.

The invention claimed is:

1. A method of producing a catechol modified chitosan dressing, comprising at least one of the following steps:
   (a) substituting chitosan with about 10% catechol;
   (b) oxidizing catechol to o-quinone and cross-linking the o-quinone in the chitosan dressing; or
   (c) freeze-drying;
   wherein the dressing has a pink to pinkish brown coloration, is hemostatic, and has a thickness that is 500 microns or less.

2. A method of producing a catechol modified chitosan dressing, comprising:
   (a) performing synthesis with chitosan and catechol in an aqueous reaction solution;
   (b) maintaining a pH of the reaction solution at or below pH 5.5;
   (c) after step (b), increasing the pH of the reaction solution, and controlling oxygen exposure to the reaction solution, to provide catechol oxidation and cross-linking; and
   (d) drying the reaction solution;
   wherein the method does not comprise an intermediate drying step between step (b) and step (c) and, optionally, wherein, in step (c), the pH of the reaction solution is increased to a range of about 5.8 to about 6.2.

* * * * *